US012774338B2

(12) United States Patent
Soga et al.

(10) Patent No.: US 12,774,338 B2
(45) Date of Patent: Oct. 27, 2026

(54) MULTISPECIFIC ANTIBODY BINDING TO ActRIIA, ActRIIB, AND Fn14

(71) Applicant: Astellas Pharma Inc., Tokyo (JP)

(72) Inventors: Shinji Soga, Tokyo (JP); Takeshi Shigenaga, Tokyo (JP); Takeshi Tsutsumi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 588 days.

(21) Appl. No.: 18/272,020

(22) PCT Filed: Jan. 12, 2022

(86) PCT No.: PCT/JP2022/000661

§ 371 (c)(1), (2) Date: Jul. 12, 2023

(87) PCT Pub. No.: WO2022/153997

PCT Pub. Date: Jul. 21, 2022

(65) Prior Publication Data

US 2024/0092916 A1 Mar. 21, 2024

(30) Foreign Application Priority Data

Jan. 13, 2021 (JP) ................................ 2021-003805

(51) Int. Cl.
*C07K 16/28* (2006.01)
*A61K 39/395* (2006.01)

(52) U.S. Cl.
CPC ........ *C07K 16/2863* (2013.01); *A61K 39/395* (2013.01); *C07K 2317/31* (2013.01); *C07K 2319/00* (2013.01)

(58) Field of Classification Search
CPC ............ C07K 16/2863; C07K 2317/31; C07K 2319/00; C07K 2317/21; C07K 2317/22; C07K 2317/24; C07K 2317/569; C07K 2317/60; C07K 2317/76; C07K 2317/92; C07K 14/71; C07K 16/2878; A61K 39/395; A61K 2039/505; C12N 15/1037; C12N 9/1205; C12P 21/02; A61P 21/00
See application file for complete search history.

(56) References Cited

U.S. PATENT DOCUMENTS

2021/0388096 A1 12/2021 Ito et al.

FOREIGN PATENT DOCUMENTS

| | | | |
|---|---|---|---|
| EP | 2 859 114 | B1 | 4/2015 |
| JP | 2016-528247 | A | 9/2016 |
| WO | WO-2010/125003 | A1 | 11/2010 |
| WO | WO-2013/026099 | A1 | 2/2013 |
| WO | WO-2015/022658 | A2 | 2/2015 |
| WO | WO-2017/081624 | A1 | 5/2017 |
| WO | WO-2019/134710 | A1 | 7/2019 |
| WO | WO-2020/090892 | A1 | 5/2020 |
| WO | WO-2020/128927 | A1 | 6/2020 |

OTHER PUBLICATIONS

Morvan et al. Proc Natl Acad Sci U S A. Nov. 21, 2017;114(47):12448-12453 (Year: 2017).*
Amato et al., "Treatment of sporadic inclusion body myositis with bimagrumab," Neurology. 2014, 83:2239-2246.
Bonaldo et al., "Cellular and molecular mechanisms of muscle atrophy," Disease Models & Mechanisms, 2013, 6:25-39.
Hanna et al., "Safety and efficacy of intravenous bimagrumab in inclusion body myotosis (RESILIENT): a randomised, double-blind, placebo-controlled phase 2b trial," Lancet Neurol., 2019, 18:834-844.
International Search Report and Written Opinion dated Mar. 22, 2022 in PCT/JP2022/000661.
Morosetti et al., "TWEAK in Inclusion-Body Myositis Muscle: Possible Pathogenic Role of a Cytokine Inhibiting Myogenesis," The Journal of American Pathology, Apr. 2012, 180(4):1603-1613.
Naddaf et al., "Inclusion Body Myositis: Update on Pathogenesis and Treatment," Neurotherapeutics, 2018, 15:995-1005.
Sato et al., "TWEAK/Fn14 signaling axis mediates skeletal muscle atrophy and metabolic dysfunction," Frontiers in Immunology, Jan. 27, 2014, 5(18):1-10.
Office Action dated Nov. 27, 2025 in JP 2022-575595, with English translation.
De Greve Henri et al: "Simplified monomeric VHH-Fc antibodies provide new opportunities for passive immunization", Current Opinion in Biotechnology, London, GB, vol. 61,Dec. 4, 2019, pp. 96-101.
Extended European Search Report issued in connection with EP Appl. No. 22739403.8 dated Oct. 28, 2024.
Frederic Morvan et al: "Blockade of activin type II receptors with a dual anti-ActRIIA/IIB antibody is critical to promote maximal skeletal muscle hypertrophy", Proceedings of the National Academy of Sciences, vol. 114, No. 47, Nov. 6, 2017 (Nov. 6, 2017), pp. 12448-12453.
Serge Muyldermans: "Nanobodies: Natural Single-Domain Antibodies", Annual Review of Biochemistry, vol. 82, No. 1,Jun. 2, 2013, pp. 775-797.
Office Action dated May 6, 2026 in EP 22739403.8.

* cited by examiner

*Primary Examiner* — Sean E Aeder
*Assistant Examiner* — Yie Chia Lee
(74) *Attorney, Agent, or Firm* — Foley & Lardner LLP

(57) ABSTRACT

[Problem] Provided is a multispecific antibody for preventing or treating amyotrophic diseases such as inclusion body myositis by binding to ActRIIA, ActRIIB, and Fn14, and inhibiting an amyotrophic action which occurs via ActRIIA, ActRIIB, and Fn14.
[Means for Solution] The present inventors have conducted studies on a multispecific antibody, and provided a multispecific antibody including a polypeptide consisting of the amino acid sequence of SEQ ID NO: 2 and a polypeptide consisting of the amino acid sequence of SEQ ID NO: 4.

15 Claims, 4 Drawing Sheets

Specification includes a Sequence Listing.

SEQUENCE LISTING

```
<160> NUMBER OF SEQ ID NOS: 18

<210> SEQ ID NO 1
<211> LENGTH: 2160
<212> TYPE: DNA
<213> ORGANISM: Artificial Sequence
<220> FEATURE:
<223> OTHER INFORMATION: NMA_75E9S81.5_h1y_HC
<220> FEATURE:
<221> NAME/KEY: CDS
<222> LOCATION: (1)..(2160)

<400> SEQUENCE: 1

gaa gtg cag ctg gtt gaa tct ggc ggc gga ttg gtt cag cct ggc gga       48
Glu Val Gln Leu Val Glu Ser Gly Gly Gly Leu Val Gln Pro Gly Gly
1               5                   10                  15

tct ctg aga ctg tct tgc gcc gcc tcc aga tcc atc ttt gcc tac ggc       96
Ser Leu Arg Leu Ser Cys Ala Ala Ser Arg Ser Ile Phe Ala Tyr Gly
            20                  25                  30

acc atg gcc tgg tac aga cag gct cct ggc aag ggc aga gaa ctg gtg      144
Thr Met Ala Trp Tyr Arg Gln Ala Pro Gly Lys Gly Arg Glu Leu Val
        35                  40                  45

gct aca atc tct ggc gga ggc acc acc tcc tac tcc gac tct gtg aag      192
```

-continued

```
Ala Thr Ile Ser Gly Gly Gly Thr Thr Ser Tyr Ser Asp Ser Val Lys
    50                  55                  60

ggc aga ttc acc atc tcc aga gac aac ggc aag tcc acc gtg tac ctg      240
Gly Arg Phe Thr Ile Ser Arg Asp Asn Gly Lys Ser Thr Val Tyr Leu
65                  70                  75                  80

cag atg aac tcc ctg aga gcc gag gac acc gcc gtg tac tac tgc aac      288
Gln Met Asn Ser Leu Arg Ala Glu Asp Thr Ala Val Tyr Tyr Cys Asn
                85                  90                  95

aag cgg tct atc ggc acc aac gat ttc tgg ggc cag ggc aca ctg gtc      336
Lys Arg Ser Ile Gly Thr Asn Asp Phe Trp Gly Gln Gly Thr Leu Val
            100                 105                 110

aca gtt tct agc gga ggc gga gga tca ggt ggc ggt gga agt ggt ggt      384
Thr Val Ser Ser Gly Gly Gly Gly Ser Gly Gly Gly Gly Ser Gly Gly
        115                 120                 125

ggc gga agt ggc ggc ggt gga tca ggc ggt ggc gga tct gaa gtt cag      432
Gly Gly Ser Gly Gly Gly Gly Ser Gly Gly Gly Gly Ser Glu Val Gln
    130                 135                 140

ctc gtg gaa agt ggc gga gga ctg gtg caa cca ggt gga agt ctg cgg      480
Leu Val Glu Ser Gly Gly Gly Leu Val Gln Pro Gly Gly Ser Leu Arg
145                 150                 155                 160

ctg tct tgt gct gcc tct ggc ttc acc ctg acc acc aac gct ctg atc      528
Leu Ser Cys Ala Ala Ser Gly Phe Thr Leu Thr Thr Asn Ala Leu Ile
                165                 170                 175

tgg ggc aga caa gct cca ggt gct gct cct gga aaa ggc cct gaa tgg      576
Trp Gly Arg Gln Ala Pro Gly Ala Ala Pro Gly Lys Gly Pro Glu Trp
            180                 185                 190

gtg gcc ggc atc aga gct gat ggc aga cct tac tac ggc gac tcc atg      624
Val Ala Gly Ile Arg Ala Asp Gly Arg Pro Tyr Tyr Gly Asp Ser Met
        195                 200                 205

aag gga aga gtg acc atc agc cgg gat atc gcc aag aac acc gcc tat      672
Lys Gly Arg Val Thr Ile Ser Arg Asp Ile Ala Lys Asn Thr Ala Tyr
    210                 215                 220

ctc cag atg aac agc ctg cgg cct gag gat aca gct gtg tac ttc tgc      720
Leu Gln Met Asn Ser Leu Arg Pro Glu Asp Thr Ala Val Tyr Phe Cys
225                 230                 235                 240

gcc acc aga ctg gac gac tct ggc acc tac gat aga ggc aga ggc aca      768
Ala Thr Arg Leu Asp Asp Ser Gly Thr Tyr Asp Arg Gly Arg Gly Thr
                245                 250                 255

acc gtg acc gtg tct agt ggc ggc gga gga agc ggc gga ggc gga agc      816
Thr Val Thr Val Ser Ser Gly Gly Gly Gly Ser Gly Gly Gly Gly Ser
            260                 265                 270

gaa gtt cag ttg gtt gag tca ggc gga ggc ctc gtg aaa cct ggc ggt      864
Glu Val Gln Leu Val Glu Ser Gly Gly Gly Leu Val Lys Pro Gly Gly
        275                 280                 285

agc ctc aga ctt tcc tgt gcc gct tct ggc atc acc ttc tcc acc tac      912
Ser Leu Arg Leu Ser Cys Ala Ala Ser Gly Ile Thr Phe Ser Thr Tyr
    290                 295                 300

ggc atg aac tgg gtc cga cag gca cca ggc aaa gga ctg gaa tgg gtg      960
Gly Met Asn Trp Val Arg Gln Ala Pro Gly Lys Gly Leu Glu Trp Val
305                 310                 315                 320

tcc tcc atc tcc tct cgg tcc atc cac atc agc tac gcc gac agc gtg     1008
Ser Ser Ile Ser Ser Arg Ser Ile His Ile Ser Tyr Ala Asp Ser Val
                325                 330                 335

aaa ggc cgg ttc acc atc agc aga gat aat gcc aaa aac tcc ctc tac     1056
Lys Gly Arg Phe Thr Ile Ser Arg Asp Asn Ala Lys Asn Ser Leu Tyr
            340                 345                 350

ttg cag atg tcc tct ctg cgg gcc gac gat act gcc gtg tat tat tgc     1104
Leu Gln Met Ser Ser Leu Arg Ala Asp Asp Thr Ala Val Tyr Tyr Cys
        355                 360                 365
```

-continued

```
gcc aga gac aga ggc gcc gct gcc ttc gat tat tgg ggc aga gga aca      1152
Ala Arg Asp Arg Gly Ala Ala Ala Phe Asp Tyr Trp Gly Arg Gly Thr
    370                 375                 380

ctg gtg gcc gtg tcc tcc gct tct acc aag gga cct tct gtg ttc cct      1200
Leu Val Ala Val Ser Ser Ala Ser Thr Lys Gly Pro Ser Val Phe Pro
385                 390                 395                 400

ctg gct ccc tcc agc aag tct act tct ggc gga aca gct gcc ctg ggc      1248
Leu Ala Pro Ser Ser Lys Ser Thr Ser Gly Gly Thr Ala Ala Leu Gly
                405                 410                 415

tgc ctg gtc aag gat tac ttt cct gag cct gtg aca gtg tcc tgg aac      1296
Cys Leu Val Lys Asp Tyr Phe Pro Glu Pro Val Thr Val Ser Trp Asn
            420                 425                 430

tct ggc gct ctg aca tct ggc gtg cac acc ttt cca gct gtg ctg cag      1344
Ser Gly Ala Leu Thr Ser Gly Val His Thr Phe Pro Ala Val Leu Gln
        435                 440                 445

tcc tct ggc ctg tac tct ctg tcc tcc gtc gtg aca gtg cct tcc agc      1392
Ser Ser Gly Leu Tyr Ser Leu Ser Ser Val Val Thr Val Pro Ser Ser
    450                 455                 460

tct ctg ggc acc cag acc tac atc tgt aat gtg aac cac aag cct tcc      1440
Ser Leu Gly Thr Gln Thr Tyr Ile Cys Asn Val Asn His Lys Pro Ser
465                 470                 475                 480

aac acc aag gtg gac aag aag gtg gaa ccc aag tcc tgc gac aag acc      1488
Asn Thr Lys Val Asp Lys Lys Val Glu Pro Lys Ser Cys Asp Lys Thr
                485                 490                 495

cac acc tgt cca cca tgt cct gct cca gaa gct gct ggc ggc cca tcc      1536
His Thr Cys Pro Pro Cys Pro Ala Pro Glu Ala Ala Gly Gly Pro Ser
            500                 505                 510

gtg ttt ctg ttc cct cca aag cct aag gac acc ctg tac atc acc cgc      1584
Val Phe Leu Phe Pro Pro Lys Pro Lys Asp Thr Leu Tyr Ile Thr Arg
        515                 520                 525

gag cct gaa gtg acc tgc gtg gtg gtc gat gtg tct cac gag gac ccc      1632
Glu Pro Glu Val Thr Cys Val Val Val Asp Val Ser His Glu Asp Pro
    530                 535                 540

gaa gtg aag ttt aat tgg tac gtg gac ggc gtc gag gtg cac aac gct      1680
Glu Val Lys Phe Asn Trp Tyr Val Asp Gly Val Glu Val His Asn Ala
545                 550                 555                 560

aag acc aag cct aga gag gaa cag tac aac agc acc tac aga gtg gtg      1728
Lys Thr Lys Pro Arg Glu Glu Gln Tyr Asn Ser Thr Tyr Arg Val Val
                565                 570                 575

tcc gtg ctg acc gtg ctg cac cag gat tgg ctg aac ggc aaa gag tac      1776
Ser Val Leu Thr Val Leu His Gln Asp Trp Leu Asn Gly Lys Glu Tyr
            580                 585                 590

aag tgc aag gtg tcc aac aag gcc ctg cct gct cct atc gaa aag acc      1824
Lys Cys Lys Val Ser Asn Lys Ala Leu Pro Ala Pro Ile Glu Lys Thr
        595                 600                 605

atc tct aag gcc aag ggc cag cct cgg gaa ccc cag gtt tac aca ttg      1872
Ile Ser Lys Ala Lys Gly Gln Pro Arg Glu Pro Gln Val Tyr Thr Leu
    610                 615                 620

cca cct tct cgg gac gag ctg acc aag aac cag gtg tcc ctg acc tgt      1920
Pro Pro Ser Arg Asp Glu Leu Thr Lys Asn Gln Val Ser Leu Thr Cys
625                 630                 635                 640

ctc gtg aag ggc ttc tac ccc tcc gat atc gcc gtg gaa tgg gag tct      1968
Leu Val Lys Gly Phe Tyr Pro Ser Asp Ile Ala Val Glu Trp Glu Ser
                645                 650                 655

aat ggc cag cca gag aac aac tac aag aca acc cct cct gtg ctg gac      2016
Asn Gly Gln Pro Glu Asn Asn Tyr Lys Thr Thr Pro Pro Val Leu Asp
            660                 665                 670

tcc gac ggc tca ttc ttt ctg tac tcc aag ctg aca gtg gac aag tcc      2064
Ser Asp Gly Ser Phe Phe Leu Tyr Ser Lys Leu Thr Val Asp Lys Ser
        675                 680                 685
```

```
aga tgg cag cag ggc aac gtg ttc tcc tgc agc gtg atg cac gag gcc     2112
Arg Trp Gln Gln Gly Asn Val Phe Ser Cys Ser Val Met His Glu Ala
    690                 695                 700

ctg cac aat cac tac acc cag aag tcc ctg tct ctg tcc cct ggc aaa     2160
Leu His Asn His Tyr Thr Gln Lys Ser Leu Ser Leu Ser Pro Gly Lys
705                 710                 715                 720


<210> SEQ ID NO 2
<211> LENGTH: 720
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Phe Ala Tyr Gly
            20                  25                  30

Thr Met Ala Trp Tyr Arg Gln Ala Pro Gly Lys Gly Arg Glu Leu Val
        35                  40                  45

Ala Thr Ile Ser Gly Gly Gly Thr Thr Ser Tyr Ser Asp Ser Val Lys
    50                  55                  60

Gly Arg Phe Thr Ile Ser Arg Asp Asn Gly Lys Ser Thr Val Tyr Leu
65                  70                  75                  80

Gln Met Asn Ser Leu Arg Ala Glu Asp Thr Ala Val Tyr Tyr Cys Asn
                85                  90                  95

Lys Arg Ser Ile Gly Thr Asn Asp Phe Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Phe Thr Leu Thr Thr Asn Ala Leu Ile
                165                 170                 175

Trp Gly Arg Gln Ala Pro Gly Ala Ala Pro Gly Lys Gly Pro Glu Trp
            180                 185                 190

Val Ala Gly Ile Arg Ala Asp Gly Arg Pro Tyr Tyr Gly Asp Ser Met
        195                 200                 205

Lys Gly Arg Val Thr Ile Ser Arg Asp Ile Ala Lys Asn Thr Ala Tyr
    210                 215                 220

Leu Gln Met Asn Ser Leu Arg Pro Glu Asp Thr Ala Val Tyr Phe Cys
225                 230                 235                 240

Ala Thr Arg Leu Asp Asp Ser Gly Thr Tyr Asp Arg Gly Arg Gly Thr
                245                 250                 255

Thr Val Thr Val Ser Ser Gly Gly Gly Gly Ser Gly Gly Gly Gly Ser
            260                 265                 270

Glu Val Gln Leu Val Glu Ser Gly Gly Gly Leu Val Lys Pro Gly Gly
        275                 280                 285

Ser Leu Arg Leu Ser Cys Ala Ala Ser Gly Ile Thr Phe Ser Thr Tyr
    290                 295                 300

Gly Met Asn Trp Val Arg Gln Ala Pro Gly Lys Gly Leu Glu Trp Val
305                 310                 315                 320
```

```
Ser Ser Ile Ser Ser Arg Ser Ile His Ile Ser Tyr Ala Asp Ser Val
                325                 330                 335

Lys Gly Arg Phe Thr Ile Ser Arg Asp Asn Ala Lys Asn Ser Leu Tyr
            340                 345                 350

Leu Gln Met Ser Ser Leu Arg Ala Asp Asp Thr Ala Val Tyr Tyr Cys
        355                 360                 365

Ala Arg Asp Arg Gly Ala Ala Ala Phe Asp Tyr Trp Gly Arg Gly Thr
    370                 375                 380

Leu Val Ala Val Ser Ser Ala Ser Thr Lys Gly Pro Ser Val Phe Pro
385                 390                 395                 400

Leu Ala Pro Ser Ser Lys Ser Thr Ser Gly Gly Thr Ala Ala Leu Gly
                405                 410                 415

Cys Leu Val Lys Asp Tyr Phe Pro Glu Pro Val Thr Val Ser Trp Asn
            420                 425                 430

Ser Gly Ala Leu Thr Ser Gly Val His Thr Phe Pro Ala Val Leu Gln
        435                 440                 445

Ser Ser Gly Leu Tyr Ser Leu Ser Ser Val Val Thr Val Pro Ser Ser
    450                 455                 460

Ser Leu Gly Thr Gln Thr Tyr Ile Cys Asn Val Asn His Lys Pro Ser
465                 470                 475                 480

Asn Thr Lys Val Asp Lys Lys Val Glu Pro Lys Ser Cys Asp Lys Thr
                485                 490                 495

His Thr Cys Pro Pro Cys Pro Ala Pro Glu Ala Ala Gly Gly Pro Ser
            500                 505                 510

Val Phe Leu Phe Pro Pro Lys Pro Lys Asp Thr Leu Tyr Ile Thr Arg
        515                 520                 525

Glu Pro Glu Val Thr Cys Val Val Val Asp Val Ser His Glu Asp Pro
    530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Asp Glu Leu Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720
```

<210> SEQ ID NO 3
<211> LENGTH: 642
<212> TYPE: DNA

```
<213> ORGANISM: Artificial Sequence
<220> FEATURE:
<223> OTHER INFORMATION: STF_8-1_h1g_LC
<220> FEATURE:
<221> NAME/KEY: CDS
<222> LOCATION: (1)..(642)

<400> SEQUENCE: 3

gcc atc cag atg acc cag tct cca tcc tct ctg tcc gcc tct gtg ggc       48
Ala Ile Gln Met Thr Gln Ser Pro Ser Ser Leu Ser Ala Ser Val Gly
1               5                   10                  15

gac aga gtg acc atc acc tgt aga gcc tct cag gcc atc tcc aac gac       96
Asp Arg Val Thr Ile Thr Cys Arg Ala Ser Gln Ala Ile Ser Asn Asp
            20                  25                  30

ctc ggc tgg tat cag cag aag cct ggc aag gct ccc aag ctg ctg atc      144
Leu Gly Trp Tyr Gln Gln Lys Pro Gly Lys Ala Pro Lys Leu Leu Ile
        35                  40                  45

tac gac gcc atc tct ctg cag tct ggc gtg ccc tct aga ttc tcc ggc      192
Tyr Asp Ala Ile Ser Leu Gln Ser Gly Val Pro Ser Arg Phe Ser Gly
    50                  55                  60

tct ggc tct ggc acc gac ttt acc ctg aca atc tcc agc ctg cag cct      240
Ser Gly Ser Gly Thr Asp Phe Thr Leu Thr Ile Ser Ser Leu Gln Pro
65                  70                  75                  80

gag gac ttc gcc acc tac tac tgc ctg caa gac ttc aac tac cct cgg      288
Glu Asp Phe Ala Thr Tyr Tyr Cys Leu Gln Asp Phe Asn Tyr Pro Arg
                85                  90                  95

acc ttt ggc cag ggc acc aag gtg gaa atc aag cgg aca gtg gcc gct      336
Thr Phe Gly Gln Gly Thr Lys Val Glu Ile Lys Arg Thr Val Ala Ala
            100                 105                 110

cct tcc gtg ttc atc ttc cca cct tcc gac gag cag ctg aag tcc ggc      384
Pro Ser Val Phe Ile Phe Pro Pro Ser Asp Glu Gln Leu Lys Ser Gly
        115                 120                 125

aca gct tct gtc gtg tgc ctg ctg aac aac ttc tac ccc aga gaa gcc      432
Thr Ala Ser Val Val Cys Leu Leu Asn Asn Phe Tyr Pro Arg Glu Ala
    130                 135                 140

aag gtg cag tgg aag gtg gac aac gca ctg cag tcc ggc aac tcc caa      480
Lys Val Gln Trp Lys Val Asp Asn Ala Leu Gln Ser Gly Asn Ser Gln
145                 150                 155                 160

gag tct gtg acc gag cag gac tcc aag gac agc acc tac agc ctg tcc      528
Glu Ser Val Thr Glu Gln Asp Ser Lys Asp Ser Thr Tyr Ser Leu Ser
                165                 170                 175

tcc aca ctg acc ctg tcc aag gcc gac tac gaa aag cac aag gtg tac      576
Ser Thr Leu Thr Leu Ser Lys Ala Asp Tyr Glu Lys His Lys Val Tyr
            180                 185                 190

gcc tgc gaa gtg acc cat cag ggc ctg tct agc cct gtg acc aag tct      624
Ala Cys Glu Val Thr His Gln Gly Leu Ser Ser Pro Val Thr Lys Ser
        195                 200                 205

ttc aac cgg ggc gag tgc                                              642
Phe Asn Arg Gly Glu Cys
    210


<210> SEQ ID NO 4
<211> LENGTH: 214
<212> TYPE: PRT
<213> ORGANISM: Artificial Sequence
<220> FEATURE:
<223> OTHER INFORMATION: Synthetic Construct

<400> SEQUENCE: 4

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Asn Asp
```

```
            20                  25                  30

Leu Gly Trp Tyr Gln Gln Lys Pro Gly Lys Ala Pro Lys Leu Leu Ile
        35                  40                  45

Tyr Asp Ala Ile Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 5
<211> LENGTH: 4
<212> TYPE: PRT
<213> ORGANISM: Artificial Sequence
<220> FEATURE:
<223> OTHER INFORMATION: Linker

<400> SEQUENCE: 5

Gly Gly Gly Ser
1


<210> SEQ ID NO 6
<211> LENGTH: 4
<212> TYPE: PRT
<213> ORGANISM: Artificial Sequence
<220> FEATURE:
<223> OTHER INFORMATION: Linker

<400> SEQUENCE: 6

Ser Gly Gly Gly
1


<210> SEQ ID NO 7
<211> LENGTH: 5
<212> TYPE: PRT
<213> ORGANISM: Artificial Sequence
<220> FEATURE:
<223> OTHER INFORMATION: Linker

<400> SEQUENCE: 7

Gly Gly Gly Gly Ser
1               5


<210> SEQ ID NO 8
```

<211> LENGTH: 5
<212> TYPE: PRT
<213> ORGANISM: Artificial Sequence
<220> FEATURE:
<223> OTHER INFORMATION: Linker

<400> SEQUENCE: 8

Ser Gly Gly Gly Gly
1 5

<210> SEQ ID NO 9
<211> LENGTH: 6
<212> TYPE: PRT
<213> ORGANISM: Artificial Sequence
<220> FEATURE:
<223> OTHER INFORMATION: Linker

<400> SEQUENCE: 9

Gly Gly Gly Gly Gly Ser
1 5

<210> SEQ ID NO 10
<211> LENGTH: 6
<212> TYPE: PRT
<213> ORGANISM: Artificial Sequence
<220> FEATURE:
<223> OTHER INFORMATION: Linker

<400> SEQUENCE: 10

Ser Gly Gly Gly Gly Gly
1 5

<210> SEQ ID NO 11
<211> LENGTH: 7
<212> TYPE: PRT
<213> ORGANISM: Artificial Sequence
<220> FEATURE:
<223> OTHER INFORMATION: Linker

<400> SEQUENCE: 11

Gly Gly Gly Gly Gly Gly Ser
1 5

<210> SEQ ID NO 12
<211> LENGTH: 7
<212> TYPE: PRT
<213> ORGANISM: Artificial Sequence
<220> FEATURE:
<223> OTHER INFORMATION: Linker

<400> SEQUENCE: 12

Ser Gly Gly Gly Gly Gly Gly
1 5

<210> SEQ ID NO 13
<211> LENGTH: 1344
<212> TYPE: DNA
<213> ORGANISM: Artificial Sequence
<220> FEATURE:
<223> OTHER INFORMATION: STF_8-1_h1g_HC
<220> FEATURE:
<221> NAME/KEY: CDS
<222> LOCATION: (1)..(1344)

<400> SEQUENCE: 13 gaa gtg cag ctg gtt gaa tct ggc ggc gga ctg gtt aag cct ggc gga 48
Glu Val Gln Leu Val Glu Ser Gly Gly Gly Leu Val Lys Pro Gly Gly
1 5 10 15

```
tct ctg aga ctg tct tgt gcc gct tcc ggc atc acc ttc tcc acc tac        96
Ser Leu Arg Leu Ser Cys Ala Ala Ser Gly Ile Thr Phe Ser Thr Tyr
            20                  25                  30

ggc atg aac tgg gtc cga cag gct cct ggc aaa ggc ctg gaa tgg gtg       144
Gly Met Asn Trp Val Arg Gln Ala Pro Gly Lys Gly Leu Glu Trp Val
        35                  40                  45

tcc tcc atc tcc agc cgg tcc atc cac atc tct tac gcc gac tcc gtg       192
Ser Ser Ile Ser Ser Arg Ser Ile His Ile Ser Tyr Ala Asp Ser Val
    50                  55                  60

aag ggc aga ttc acc atc agc cgg gac aac gcc aag aac tcc ctg tac       240
Lys Gly Arg Phe Thr Ile Ser Arg Asp Asn Ala Lys Asn Ser Leu Tyr
65                  70                  75                  80

ctg cag atg tcc agc ctg aga gcc gat gac acc gcc gtg tac tac tgc       288
Leu Gln Met Ser Ser Leu Arg Ala Asp Asp Thr Ala Val Tyr Tyr Cys
                85                  90                  95

gcc aga gat aga ggc gcc gct gcc ttc gat tat tgg ggc aga gga aca       336
Ala Arg Asp Arg Gly Ala Ala Ala Phe Asp Tyr Trp Gly Arg Gly Thr
            100                 105                 110

ctg gtg gcc gtg tcc tct gct tcc acc aag gga cct tcc gtg ttt ccc       384
Leu Val Ala Val Ser Ser Ala Ser Thr Lys Gly Pro Ser Val Phe Pro
        115                 120                 125

ctg gct cct tcc agc aag tct acc tct ggt ggc aca gct gct ctg ggc       432
Leu Ala Pro Ser Ser Lys Ser Thr Ser Gly Gly Thr Ala Ala Leu Gly
    130                 135                 140

tgc ctg gtc aag gat tac ttc cct gag cct gtg acc gtg tcc tgg aac       480
Cys Leu Val Lys Asp Tyr Phe Pro Glu Pro Val Thr Val Ser Trp Asn
145                 150                 155                 160

tct ggc gct ctg aca tct ggc gtg cac acc ttt cca gct gtg ctg cag       528
Ser Gly Ala Leu Thr Ser Gly Val His Thr Phe Pro Ala Val Leu Gln
                165                 170                 175

tcc tcc ggc ctg tac tct ctg tcc tct gtc gtg acc gtg cct tcc agc       576
Ser Ser Gly Leu Tyr Ser Leu Ser Ser Val Val Thr Val Pro Ser Ser
            180                 185                 190

tct ctg gga acc cag acc tac atc tgc aat gtg aac cac aag cct tcc       624
Ser Leu Gly Thr Gln Thr Tyr Ile Cys Asn Val Asn His Lys Pro Ser
        195                 200                 205

aac acc aag gtg gac aag aag gtg gaa ccc aag tcc tgc gac aag acc       672
Asn Thr Lys Val Asp Lys Lys Val Glu Pro Lys Ser Cys Asp Lys Thr
    210                 215                 220

cac acc tgt cca cca tgt cct gct cca gaa gct gct ggc ggc cct tct       720
His Thr Cys Pro Pro Cys Pro Ala Pro Glu Ala Ala Gly Gly Pro Ser
225                 230                 235                 240

gtg ttt ctg ttc cct cca aag cct aag gac acc ctg atg atc tct cgg       768
Val Phe Leu Phe Pro Pro Lys Pro Lys Asp Thr Leu Met Ile Ser Arg
                245                 250                 255

acc cct gaa gtg acc tgc gtg gtg gtg gat gtg tct cac gag gat ccc       816
Thr Pro Glu Val Thr Cys Val Val Val Asp Val Ser His Glu Asp Pro
            260                 265                 270

gaa gtg aag ttc aat tgg tac gtg gac ggc gtg gaa gtg cac aat gcc       864
Glu Val Lys Phe Asn Trp Tyr Val Asp Gly Val Glu Val His Asn Ala
        275                 280                 285

aag acc aag cct aga gag gaa cag tac aac agc acc tac aga gtg gtg       912
Lys Thr Lys Pro Arg Glu Glu Gln Tyr Asn Ser Thr Tyr Arg Val Val
    290                 295                 300

tcc gtg ctg acc gtg ctg cac cag gat tgg ctg aac ggc aaa gag tac       960
Ser Val Leu Thr Val Leu His Gln Asp Trp Leu Asn Gly Lys Glu Tyr
305                 310                 315                 320

aag tgc aag gtg tcc aac aag gcc ctg cct gct cct atc gaa aag acc      1008
Lys Cys Lys Val Ser Asn Lys Ala Leu Pro Ala Pro Ile Glu Lys Thr
```

```
                325                 330                 335

atc tcc aag gcc aag ggc cag cct agg gaa ccc cag gtt tac acc ttg     1056
Ile Ser Lys Ala Lys Gly Gln Pro Arg Glu Pro Gln Val Tyr Thr Leu
            340                 345                 350

cca cct tct cgg gac gag ctg acc aag aac cag gtg tcc ctg acc tgc     1104
Pro Pro Ser Arg Asp Glu Leu Thr Lys Asn Gln Val Ser Leu Thr Cys
        355                 360                 365

ctc gtg aag gga ttc tac ccc tcc gat atc gcc gtg gaa tgg gag tct     1152
Leu Val Lys Gly Phe Tyr Pro Ser Asp Ile Ala Val Glu Trp Glu Ser
    370                 375                 380

aat ggc cag cca gag aac aac tac aag aca acc cct cct gtg ctg gac     1200
Asn Gly Gln Pro Glu Asn Asn Tyr Lys Thr Thr Pro Pro Val Leu Asp
385                 390                 395                 400

tcc gac ggc tca ttc ttt ctg tac tcc aag ctg aca gtg gac aag tcc     1248
Ser Asp Gly Ser Phe Phe Leu Tyr Ser Lys Leu Thr Val Asp Lys Ser
                405                 410                 415

aga tgg cag cag ggc aac gtg ttc tcc tgc agc gtg atg cac gag gcc     1296
Arg Trp Gln Gln Gly Asn Val Phe Ser Cys Ser Val Met His Glu Ala
            420                 425                 430

ctg cac aat cac tac acc cag aag tcc ctg tct ctg tcc cct ggc aag     1344
Leu His Asn His Tyr Thr Gln Lys Ser Leu Ser Leu Ser Pro Gly Lys
        435                 440                 445


<210> SEQ ID NO 14
<211> LENGTH: 448
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Ile Thr Phe Ser Thr Tyr
            20                  25                  30

Gly Met Asn Trp Val Arg Gln Ala Pro Gly Lys Gly Leu Glu Trp Val
        35                  40                  45

Ser Ser Ile Ser Ser Arg Ser Ile His Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Asp Asp Thr Ala Val Tyr Tyr Cys
                85                  90                  95

Ala Arg Asp Arg Gly Ala Ala Ala Phe Asp Tyr Trp Gly Arg Gly Thr
            100                 105                 110

Leu Val Ala Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 15
<211> LENGTH: 489
<212> TYPE: PRT
<213> ORGANISM: Artificial Sequence
<220> FEATURE:
<223> OTHER INFORMATION: NMA_75E9.2_m10_HC

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Phe Ala Tyr Gly
            20                  25                  30

Thr Met Ala Trp Tyr Arg Gln Ala Pro Gly Lys Gln Arg Glu Leu Val
        35                  40                  45

Ala Thr Ile Ser Gly Gly Gly Thr Thr Ser Tyr Ser Asp Ser Val Lys
    50                  55                  60

Gly Arg Phe Thr Ile Ser Arg Asp Asn Gly Lys Ser Thr Val Tyr Leu
65                  70                  75                  80

Gln Met Ser Ser Leu Lys Pro Glu Asp Thr Ala Val Tyr Tyr Cys Asn
                85                  90                  95

Lys Arg Ser Ile Gly Thr Asn Asp Phe Trp Gly Gln Gly Thr Gln Val
            100                 105                 110

Thr Val Ser Ser Gly Gly Gly Gly Ser Gly Gly Gly Gly Ser Gly Gly
        115                 120                 125
```

```
Gly Gly Ser Gly Gly Gly Gly Ser Gly Gly Gly Gly Ser Gln Val Gln
    130                 135                 140

Leu Val Glu Ser Gly Gly Gly Leu Val Gln Thr Gly Gly Ser Leu Thr
145                 150                 155                 160

Leu Ser Cys Ala Ala Ser Gly Phe Thr Leu Thr Thr Asn Ala Leu Ile
                165                 170                 175

Trp Gly Arg Gln Ala Pro Gly Ala Ala Pro Gly Glu Gly Pro Glu Trp
            180                 185                 190

Val Ala Gly Ile Arg Ala Asp Gly Arg Pro Tyr Tyr Gly Asp Ser Met
        195                 200                 205

Lys Gly Arg Val Thr Val Ser Arg Asp Ile Ala Lys Asn Thr Ala Tyr
    210                 215                 220

Leu Gln Met Thr Asn Leu Lys Pro Glu Asp Thr Ala Val Tyr Phe Cys
225                 230                 235                 240

Ala Thr Arg Leu Asp Asp Ser Gly Thr Tyr Asp Arg Gly Arg Gly Thr
                245                 250                 255

Gln Val Thr Val Ser Ser Val Pro Arg Asp Ser Gly Cys Lys Pro Cys
            260                 265                 270

Ile Cys Thr Val Pro Glu Val Ser Ser Val Phe Ile Phe Pro Pro Lys
        275                 280                 285

Pro Lys Asp Val Leu Thr Ile Thr Leu Thr Pro Lys Val Thr Cys Val
    290                 295                 300

Val Val Asp Ile Ser Lys Asp Asp Pro Glu Val Gln Phe Ser Trp Phe
305                 310                 315                 320

Val Asp Asp Val Glu Val His Thr Ala Gln Thr Lys Pro Arg Glu Glu
                325                 330                 335

Gln Phe Asn Ser Thr Phe Arg Ser Val Ser Glu Leu Pro Ile Met His
            340                 345                 350

Gln Asp Trp Leu Asn Gly Lys Glu Phe Lys Cys Arg Val Asn Ser Ala
        355                 360                 365

Ala Phe Pro Ala Pro Ile Glu Lys Thr Ile Ser Lys Thr Lys Gly Arg
    370                 375                 380

Pro Lys Ala Pro Gln Val Tyr Thr Ile Pro Pro Pro Lys Glu Gln Met
385                 390                 395                 400

Ala Lys Asp Lys Val Ser Leu Thr Cys Met Ile Thr Asp Phe Phe Pro
                405                 410                 415

Glu Asp Ile Thr Val Glu Trp Gln Trp Asn Gly Gln Pro Ala Glu Asn
            420                 425                 430

Tyr Lys Asn Thr Gln Pro Ile Met Asp Thr Asp Gly Ser Tyr Phe Val
        435                 440                 445

Tyr Ser Lys Leu Asn Val Gln Lys Ser Asn Trp Glu Ala Gly Asn Thr
    450                 455                 460

Phe Thr Cys Ser Val Leu His Glu Gly Leu His Asn His His Thr Glu
465                 470                 475                 480

Lys Ser Leu Ser His Ser Pro Gly Lys
                485
```

<210> SEQ ID NO 16
<211> LENGTH: 442
<212> TYPE: PRT
<213> ORGANISM: Artificial Sequence
<220> FEATURE:
<223> OTHER INFORMATION: STF_8-1.2_m10_HC

<400> SEQUENCE: 16

-continued

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Ile Thr Phe Ser Thr Tyr
            20                  25                  30

Gly Met Asn Trp Val Arg Gln Ala Pro Gly Lys Gly Leu Glu Trp Val
        35                  40                  45

Ser Ser Ile Ser Ser Arg Ser Ile His Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Asp Asp Thr Ala Val Tyr Tyr Cys
                85                  90                  95

Ala Arg Asp Arg Gly Ala Ala Ala Phe Asp Tyr Trp Gly Arg Gly Thr
            100                 105                 110

Leu Val Ala Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Gln Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Lys Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
```

```
            420                 425                 430

Glu Lys Ser Leu Ser His Ser Pro Gly Lys
        435                 440


<210> SEQ ID NO 17
<211> LENGTH: 214
<212> TYPE: PRT
<213> ORGANISM: Artificial Sequence
<220> FEATURE:
<223> OTHER INFORMATION: STF_8-1.2_m10_LC

<400> SEQUENCE: 17

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Asn Asp
            20                  25                  30

Leu Gly Trp Tyr Gln Gln Lys Pro Gly Lys Ala Pro Lys Leu Leu Ile
        35                  40                  45

Tyr Asp Ala Ile Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Arg
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 18
<211> LENGTH: 714
<212> TYPE: PRT
<213> ORGANISM: Artificial Sequence
<220> FEATURE:
<223> OTHER INFORMATION: NMA_75E9STF8-1_m10_HC

<400> SEQUENCE: 18

Gln Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Phe Ala Tyr Gly
            20                  25                  30

Thr Met Ala Trp Tyr Arg Gln Ala Pro Gly Lys Gln Arg Glu Leu Val
        35                  40                  45

Ala Thr Ile Ser Gly Gly Gly Thr Thr Ser Tyr Ser Asp Ser Val Lys
    50                  55                  60
```

```
Gly Arg Phe Thr Ile Ser Arg Asp Asn Gly Lys Ser Thr Val Tyr Leu
65                  70                  75                  80

Gln Met Ser Ser Leu Lys Pro Glu Asp Thr Ala Val Tyr Tyr Cys Asn
                85                  90                  95

Lys Arg Ser Ile Gly Thr Asn Asp Phe Trp Gly Gln Gly Thr Gln Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Gly Gly Gly Gly Ser Gln Val Gln
    130                 135                 140

Leu Val Glu Ser Gly Gly Gly Leu Val Gln Thr Gly Gly Ser Leu Thr
145                 150                 155                 160

Leu Ser Cys Ala Ala Ser Gly Phe Thr Leu Thr Thr Asn Ala Leu Ile
                165                 170                 175

Trp Gly Arg Gln Ala Pro Gly Ala Ala Pro Gly Glu Gly Pro Glu Trp
            180                 185                 190

Val Ala Gly Ile Arg Ala Asp Gly Arg Pro Tyr Tyr Gly Asp Ser Met
        195                 200                 205

Lys Gly Arg Val Thr Val Ser Arg Asp Ile Ala Lys Asn Thr Ala Tyr
    210                 215                 220

Leu Gln Met Thr Asn Leu Lys Pro Glu Asp Thr Ala Val Tyr Phe Cys
225                 230                 235                 240

Ala Thr Arg Leu Asp Asp Ser Gly Thr Tyr Asp Arg Gly Arg Gly Thr
                245                 250                 255

Gln Val Thr Val Ser Ser Gly Gly Gly Gly Ser Gly Gly Gly Gly Ser
            260                 265                 270

Glu Val Gln Leu Val Glu Ser Gly Gly Gly Leu Val Lys Pro Gly Gly
        275                 280                 285

Ser Leu Arg Leu Ser Cys Ala Ala Ser Gly Ile Thr Phe Ser Thr Tyr
    290                 295                 300

Gly Met Asn Trp Val Arg Gln Ala Pro Gly Lys Gly Leu Glu Trp Val
305                 310                 315                 320

Ser Ser Ile Ser Ser Arg Ser Ile His Ile Ser Tyr Ala Asp Ser Val
                325                 330                 335

Lys Gly Arg Phe Thr Ile Ser Arg Asp Asn Ala Lys Asn Ser Leu Tyr
            340                 345                 350

Leu Gln Met Ser Ser Leu Arg Ala Asp Asp Thr Ala Val Tyr Tyr Cys
        355                 360                 365

Ala Arg Asp Arg Gly Ala Ala Ala Phe Asp Tyr Trp Gly Arg Gly Thr
    370                 375                 380

Leu Val Ala Val Ser Ser Ala Lys Thr Thr Pro Pro Ser Val Tyr Pro
385                 390                 395                 400

Leu Ala Pro Gly Ser Ala Ala Gln Thr Asn Ser Met Val Thr Leu Gly
                405                 410                 415

Cys Leu Val Lys Gly Tyr Phe Pro Glu Pro Val Thr Val Thr Trp Asn
            420                 425                 430

Ser Gly Ser Leu Ser Ser Gly Val His Thr Phe Pro Ala Val Leu Gln
        435                 440                 445

Ser Asp Leu Tyr Thr Leu Ser Ser Ser Val Thr Val Pro Ser Ser Thr
    450                 455                 460

Trp Pro Ser Gln Thr Val Thr Cys Asn Val Ala His Pro Ala Ser Ser
465                 470                 475                 480

Thr Lys Val Asp Lys Lys Ile Val Pro Arg Asp Cys Gly Cys Lys Pro
```

-continued

```
                485                 490                 495

Cys Ile Cys Thr Val Pro Glu Val Ser Ser Val Phe Ile Phe Pro Pro
            500                 505                 510

Lys Pro Lys Asp Val Leu Thr Ile Thr Leu Thr Pro Lys Val Thr Cys
        515                 520                 525

Val Val Val Asp Ile Ser Lys Asp Asp Pro Glu Val Gln Phe Ser Trp
    530                 535                 540

Phe Val Asp Asp Val Glu Val His Thr Ala Gln Thr Lys Pro Arg Glu
545                 550                 555                 560

Glu Gln Phe Asn Ser Thr Phe Arg Ser Val Ser Glu Leu Pro Ile Met
                565                 570                 575

His Gln Asp Trp Leu Asn Gly Lys Glu Phe Lys Cys Arg Val Asn Ser
            580                 585                 590

Ala Ala Phe Pro Ala Pro Ile Glu Lys Thr Ile Ser Lys Thr Lys Gly
        595                 600                 605

Arg Pro Lys Ala Pro Gln Val Tyr Thr Ile Pro Pro Pro Lys Glu Gln
    610                 615                 620

Met Ala Lys Asp Lys Val Ser Leu Thr Cys Met Ile Thr Asp Phe Phe
625                 630                 635                 640

Pro Glu Asp Ile Thr Val Glu Trp Gln Trp Asn Gly Gln Pro Ala Glu
                645                 650                 655

Asn Tyr Lys Asn Thr Gln Pro Ile Met Asp Thr Asp Gly Ser Tyr Phe
            660                 665                 670

Val Tyr Ser Lys Leu Asn Val Gln Lys Ser Asn Trp Glu Ala Gly Asn
        675                 680                 685

Thr Phe Thr Cys Ser Val Leu His Glu Gly Leu His Asn His His Thr
    690                 695                 700

Glu Lys Ser Leu Ser His Ser Pro Gly Lys
705                 710
```

MULTISPECIFIC ANTIBODY BINDING TO ActRIIA, ActRIIB, AND Fn14

CROSS-REFERENCE TO RELATED APPLICATIONS

This application is the U.S. National Stage of PCT/JP2022/000661, filed Jan. 12, 2022, which claims priority to JP 2021-003805, filed Jan. 13, 2021.

The instant application contains a Sequence Listing which has been submitted in ASCII format and is hereby incorporated by reference in its entirety. Said ASCII copy, created on Jul. 12, 2023, is named sequence.txt and is 50,299 bytes.

TECHNICAL FIELD

The present invention relates to a multispecific antibody binding to ActRIIA, ActRIIB, and Fn14.

BACKGROUND ART

An activin receptor type 2A (ActRIIA) and an activin receptor type 2B (ActRIIB) are known as receptors for a myostatin and an activin A. Stimulation of ligands to ActRIIA and ActRIIB results in phosphorylation of Smad2 and Smad3. It is known that the phosphorylated Smad2/3 forms a complex with Smad4 and binds to various transcription factors to regulate gene expression (Tsuchida K et al., Endocr J. 2008, Vol. 55, p. 11-21). It is known that in the skeletal muscles, ActRIIA and ActRIIB are involved in proteolysis (Morvan F et al., Proc Natl Acad Sci USA. 2017, vol. 114, p. 12448-12453).

Fibroblast growth factor-inducible 14 (Fn14) (also referred to as TNFRSF12A) is a member of a tumor necrosis factor receptor superfamily. In addition, Fn14 is also known as a TWEAK receptor of a TNF-like weak inducer of apoptosis (TWEAK). Fn14 has TWEAK-dependent activation triggered by the binding of TWEAK and TWEAK-independent activation triggered in the absence of TWEAK. Any of the TWEAK-dependent and TWEAK-independent activations of Fn14 are known to activate an NF-κB signaling pathway and to control cell proliferation, migration, differentiation, and apoptosis, as well as inflammation involved in angiogenesis, tissue damage, and regeneration (Winkles J A, Nat Rev Drug Discov. 2008, Vol. 7, p. 411-425). With regard to the skeletal muscles, it has been reported that the expression of Fn14 increases during pathological conditions and is involved in skeletal muscle atrophy (Non-Patent Document 1). Development of several antibodies binding to Fn14 has hitherto been reported. Many of these antibodies are known to have an antagonistic activity against the activation of Fn14 induced by TWEAK stimulation (hereinafter also simply referred to as an “antagonistic activity”) and an agonistic activity of activating Fn14 in the absence of TWEAK (hereinafter simply an “agonistic activity”) at the same time. A mouse monoclonal antibody, CRCBT-06-002, has been reported to have an antagonistic activity of inhibiting IL-8 production induced by TWEAK stimulation in human malignant melanoma-derived cell line A375 cells. However, it has also been reported to have an agonistic activity of inducing IL-8 production from A375 cells in the absence of TWEAK at the same time (Patent Document 1). In recent years, an antibody binding to Fn14, which has an antagonistic activity but has no agonistic activity, is also known (Patent Document 2).

It has been reported that several factors other than ActRIIA, ActRIIB, and Fn14 are involved in skeletal muscle atrophy (Non-Patent Document 2). A tumor necrosis factor (TNF)α is involved in the degradation of skeletal muscle proteins via a TNF receptor. Glucocorticoids are also involved in the degradation of the skeletal muscle proteins via a glucocorticoid receptor. Skeletal muscle atrophy also occurs due to the suppression of an insulin-like growth factor involved in protein assimilation of skeletal muscles.

Sporadic inclusion body myositis (sIBM) is a chronic progressive muscle disease. Muscle atrophy and muscle weakness are observed mainly in quadriceps femoris muscles or finger or wrist flexors. Characteristic findings of the disease include expression of myofibers accompanied by rimmed vacuoles, and mononuclear cell infiltration or envelopment in non-necrotic myofibers orendomysium. As the disease progresses, decreased walking functions and dysphagia are observed, and the quality of life (QOL) is significantly deteriorated. However, there is currently no established treatment for sIBM (Non-Patent Document 3).

A number of clinical trials on myostatin inhibitors or ActRIIA and ActRIIB inhibitors for muscle diseases have been carried out. Among those, Bimagrumab (Patent Document 3), which is an ActRIIA and ActRIIB inhibitory antibody, is a drug, of which development has been advanced to the highest level, and a Phase II B/Phase III trial has been carried out for sIBM. Although an increase in lean body weight was observed in the Phase II B/Phase III trial of Bimagrumab, an improvement in the primary endpoint of a 6-minute walking distance was not observed (Non-Patent Document 4).

An increase in phosphorylation of Smad2 is observed in the skeletal muscle of an sIBM patient, suggesting the involvement of ActRIIA and ActRIIB stimulation in muscle atrophy (Non-Patent Document 5). In addition, it has been reported that the expression of Fn14 is elevated in the skeletal muscle of an sIBM patient (Non-Patent Document 6). However, no therapeutic agent for sIBM, targeting the inhibition of both pathways of ActRIIA and ActRIIB, and Fn14, has hitherto been reported.

CITATION LIST

Patent Literature

[Patent Document 1] International Publication No. 2013/026099

[Patent Document 2] International Publication No. 2020/090892

[Patent Document 3] International Publication No. 2017/081624

Non-Patent Literature

[Non-Patent Document 1] Sato S et al., Front Immunol. (CH) 2014, Vol. 5, Article 18

[Non-Patent Document 2] Bonald P et al., Dis Model Mech. (GB) 2013, Vol. 6, p. 25-39

[Non-Patent Document 3] Naddaf E et al., Neurotherapeutics. (US) 2018, Vol. 15, p. 995-1005

[Non-Patent Document 4] Hanna M G et al., Lancet Neurol. (GB) 2019, Vol. 18, p. 834-844

[Non-Patent Document 5] Amato A A et al., Neurology. (US) 2014, Vol. 83, p. 2239-2246

[Non-Patent Document 6] Morosetti R et al., Am J Pathol. (US) 2012, Vol. 180, p. 1603-1613

SUMMARY OF INVENTION

Technical Problem

An object of the present invention is to provide a multispecific antibody which is expected to prevent or treat amyotrophic diseases such as inclusion body myositis by binding to ActRIIA, ActRIIB, and Fn14, and inhibiting an amyotrophic action which occurs via ActRIIA, ActRIIB, and Fn14.

Solution to Problem

The present inventors have conducted repeated studies with considerable ingenuity in the development of a multispecific antibody, and as a result, they have developed a polypeptide binding to ActRIIA and ActRIIB, in which the polypeptide includes a first VHH including CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 105 of SEQ ID NO: 2, and a second VHH including CDR1 consisting of the amino acid sequence of amino acid numbers 172 to 176 of SEQ ID NO: 2, CDR2 consisting of the amino acid sequence of amino acid numbers 195 to 210 of SEQ ID NO: 2, and CDR3 consisting of the amino acid sequence of amino acid numbers 243 to 251 of SEQ ID NO: 2 (Example 2). Furthermore, the present inventors have developed a multispecific antibody in which the C terminal of the polypeptide is linked to the N terminal of a heavy chain variable region of an antibody binding to human Fn14 via a peptide linker (Examples 3 and 4). The multispecific antibody binds to ActRIIA, ActRIIB, and Fn14 (Example 5), inhibits phosphorylation of Smad induced by myostatin stimulation (Example 6), inhibits activation of NF-κB induced by TWEAK stimulation (Example 7), and does not induce activation of NF-κB in the absence of TWEAK (Example 7). As a result, the present inventors have provided the multispecific antibody that binds to ActRIIA, ActRIIB, and Fn14, thereby completing the present invention.

According to the present invention, for example, the following inventions are provided.

[1] A multispecific antibody binding to ActRIIA, ActRIIB, and Fn14, the multispecific antibody including:

(a) a polypeptide including a first VHH and a second VHH, the polypeptide binding to ActRIIA and ActRIIB; and (b) an antibody binding to Fn14 or an antigen-binding fragment thereof, in which the first VHH includes CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 105 of SEQ ID NO: 2, the second VHH includes CDR1 consisting of the amino acid sequence of amino acid numbers 172 to 176 of SEQ ID NO: 2, CDR2 consisting of the amino acid sequence of amino acid numbers 195 to 210 of SEQ ID NO: 2, and CDR3 consisting of the amino acid sequence of amino acid numbers 243 to 251 of SEQ ID NO: 2, and a C terminal of the polypeptide of (a) is linked to an N terminal of a heavy chain variable region of the antibody binding to Fn14 or an antigen-binding fragment thereof via a peptide linker.

[2] The multispecific antibody according to [1], in which the first VHH consists of the amino acid sequence of amino acid numbers 1 to 116 of SEQ ID NO: 2 and the second VHH consists of the amino acid sequence of amino acid numbers 142 to 262 of SEQ ID NO: 2.

[3] The multispecific antibody according to [1] or [2], in which a C terminal of the first VHH is linked to an N terminal of the second VHH via a peptide linker.

[4] The multispecific antibody according to [1], in which the polypeptide of (a) consists of the amino acid sequence of amino acid numbers 1 to 262 of SEQ ID NO: 2.

[5] The multispecific antibody according to any one of [1] to [4], in which the antibody binding to Fn14 or an antigen-binding fragment thereof includes a heavy chain variable region including CDR1 consisting of the amino acid sequence of amino acid numbers 303 to 307 of SEQ ID NO: 2, CDR2 consisting of the amino acid sequence of amino acid numbers 322 to 338 of SEQ ID NO: 2, and CDR3 consisting of the amino acid sequence of amino acid numbers 371 to 379 of SEQ ID NO: 2, and a light chain variable region including CDR1 consisting of the amino acid sequence of amino acid numbers 24 to 34 of SEQ ID NO: 4, CDR2 consisting of the amino acid sequence of amino acid numbers 50 to 56 of SEQ ID NO: 4, and CDR3 consisting of the amino acid sequence of amino acid numbers 89 to 97 of SEQ ID NO: 4.

[6] The multispecific antibody according to any one of [1] to [4], in which the antibody binding to Fn14 or an antigen-binding fragment thereof includes a heavy chain variable region consisting of the amino acid sequence of amino acid numbers 273 to 390 of SEQ ID NO: 2 and a light chain variable region consisting of the amino acid sequence of amino acid numbers 1 to 108 of SEQ ID NO: 4.

[7] The multispecific antibody according to any one of [1] to [6], in which the multispecific antibody includes an antibody binding to Fn14, and the antibody binding to Fn14 includes a heavy chain constant region having amino acid mutations of L234A, L235A, M252Y, S254T, and T256E.

[8] The multispecific antibody according to any one of [1] to [4], in which the multispecific antibody includes an antibody binding to Fn14, and the antibody binding to Fn14 includes a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E, and a light chain including a light chain variable region consisting of the amino acid sequence of amino acid numbers 1 to 108 of SEQ ID NO: 4 and a light chain constant region.

[9] The multispecific antibody according to any one of [1] to [4], in which the multispecific antibody includes an antibody binding to Fn14, and the antibody binding to Fn14 or an antigen-binding fragment thereof includes a heavy chain consisting of the amino acid sequence of amino acid numbers 273 to 720 of SEQ ID NO: 2 and a light chain consisting of the amino acid sequence of SEQ ID NO: 4.

[10] The multispecific antibody according to [1], in which the multispecific antibody includes a polypeptide consisting of the amino acid sequence of SEQ ID NO: 2 and a light chain consisting of the amino acid sequence of SEQ ID NO: 4.

[11] The multispecific antibody according to any one of [1] to [10], wherein the multispecific antibody is post-translationally modified.

[12] A polynucleotide including a nucleotide sequence encoding the polypeptide of (a) in the multispecific antibody according to any one of [1] to [4].

[13] Apolynucleotide including a nucleotide sequence encoding the heavy chain variable region of the antibody binding to Fn14 or an antigen-binding fragment thereof in the multispecific antibody according to any one of [5] to [9].

[14] Apolynucleotide including a nucleotide sequence encoding the light chain variable region of the antibody binding to Fn14 or an antigen-binding fragment thereof in the multispecific antibody according to any one of [5] to [9].

[15] A polynucleotide including a nucleotide sequence encoding the polypeptide of (a) and the polypeptide including the heavy chain variable region of the antibody binding to Fn14 or an antigen-binding fragment thereof in the multispecific antibody according to any one of [1] to [9].

[16] A polynucleotide including a nucleotide sequence encoding the polypeptide in the multispecific antibody according to [10].

[17] A polynucleotide including a nucleotide sequence encoding the light chain of the multispecific antibody according to [10].

[18] An expression vector including the polynucleotide according to any one of [12] to [15].

[19] An expression vector including the polynucleotide according to [14] and/or [15].

[20] An expression vector including the polynucleotide according to [16] and/or [17].

[21] A host cell transfected with the expression vector including the polynucleotide according to any one of [18] to [20].

[22] A host cell transfected with an expression vector including the following polynucleotides of (i) and (ii), or transfected with an expression vector including the following polynucleotide of (i) and/or an expression vector including the following polynucleotide of (ii):

(i) a polynucleotide including a nucleotide sequence encoding a polypeptide including the light chain variable region of the antibody binding to Fn14 or an antigen-binding fragment thereof in the multispecific antibody according to any one of [1] to [9];

(ii) a polynucleotide including a nucleotide sequence encoding the polypeptide of (a) and the polypeptide including the heavy chain variable region of the antibody binding to Fn14 or an antigen-binding fragment thereof in the multispecific antibody according to any one of [1] to [9].

[23] A host cell selected from the group consisting of the following (A) to (D):

(A) a host cell transfected with an expression vector including a polynucleotide including a nucleotide sequence encoding the polypeptide in the multispecific antibody according to [10] and a polynucleotide including a nucleotide sequence encoding the light chain of the multispecific antibody according to [10];

(B) a host cell transfected with an expression vector including a polynucleotide including a nucleotide sequence encoding the polypeptide in the multispecific antibody according to [10] and an expression vector including a polynucleotide including a nucleotide sequence encoding the light chain of the multispecific antibody according to [10];

(C) a host cell transfected with an expression vector including a polynucleotide including a nucleotide sequence encoding the polypeptide in the multispecific antibody according to [10]; and (D) a host cell transfected with an expression vector including a polynucleotide including a nucleotide sequence encoding the light chain of the multispecific antibody according to [10].

[24] A method for producing a multispecific antibody binding to ActRIIA, ActRIIB, and Fn14, the method including a step of culturing a host cell transfected with an expression vector including the following polynucleotides of (i) and (ii), or an expression vector including the following polynucleotide of (i) and an expression vector including the following polynucleotide of (ii) to express the multispecific antibody:

(i) a polynucleotide including a nucleotide sequence encoding a polypeptide including the light chain variable region of the antibody binding to Fn14 or an antigen-binding fragment thereof in the multispecific antibody according to any one of [1] to [9];

(ii) a polynucleotide including a nucleotide sequence encoding the polypeptide of (a) and the polypeptide including the heavy chain variable region of the antibody binding to Fn14 or an antigen-binding fragment thereof in the multispecific antibody according to any one of [1] to [9].

[25] A method for producing a multispecific antibody binding to ActRIIA, ActRIIB, and Fn14, the method including a step of culturing a host cell selected from the group consisting of the following (E) to (G) to express the multispecific antibody:

(E) a host cell transfected with an expression vector including a polynucleotide including a nucleotide sequence encoding the polypeptide in the multispecific antibody according to [10] and a polynucleotide including a nucleotide sequence encoding the light chain of the multispecific antibody according to [10];

(F) a host cell transfected with an expression vector including a polynucleotide including a nucleotide sequence encoding the polypeptide in the multispecific antibody according to [10] and an expression vector including a polynucleotide including a nucleotide sequence encoding the light chain of the multispecific antibody according to [10]; and (G) a host cell transfected with an expression vector including a polynucleotide including a nucleotide sequence encoding the polypeptide in the multispecific antibody according to [10] and a host cell transfected with an expression vector including a polynucleotide including a nucleotide sequence encoding the light chain of the multispecific antibody according to [10].

[26] A multispecific antibody produced by the method according to [24].

[27] A multispecific antibody produced by the method according to [25].

[28] A pharmaceutical composition including:

the multispecific antibody according to any one of [1] to [11], [26], and [27]; and a pharmaceutically acceptable excipient.

[29] The pharmaceutical composition according to [28], in which the pharmaceutical composition is a pharmaceutical composition for preventing or treating inclusion body myositis.

[30] A method for preventing or treating inclusion body myositis, the method including administering a therapeutically effective amount of the multispecific antibody according to any one of [1] to [11], [26], and [27].

[31] The multispecific antibody according to any one of [1] to [11], [26], and [27], in which the multispecific antibody is for use in prevention or treatment of inclusion body myositis.

[32] A use of the multispecific antibody according to any one of [1] to [11], [26], and [27] in production of a pharmaceutical composition for preventing or treating inclusion body myositis.

Advantageous Effects of Invention

The multispecific antibody of the present invention is expected to inhibit phosphorylation of Smad induced by myostatin stimulation and to inhibit activation of Fn14 induced by TWEAK stimulation without exhibiting an agonistic activity, thereby being provided with a muscle atrophy suppressing action. Furthermore, there is a possibility that the multispecific antibody can be used as a prophylactic or therapeutic agent for amyotrophic diseases such as inclusion body myositis.

DESCRIPTION OF EMBODIMENTS

Figure 1A:
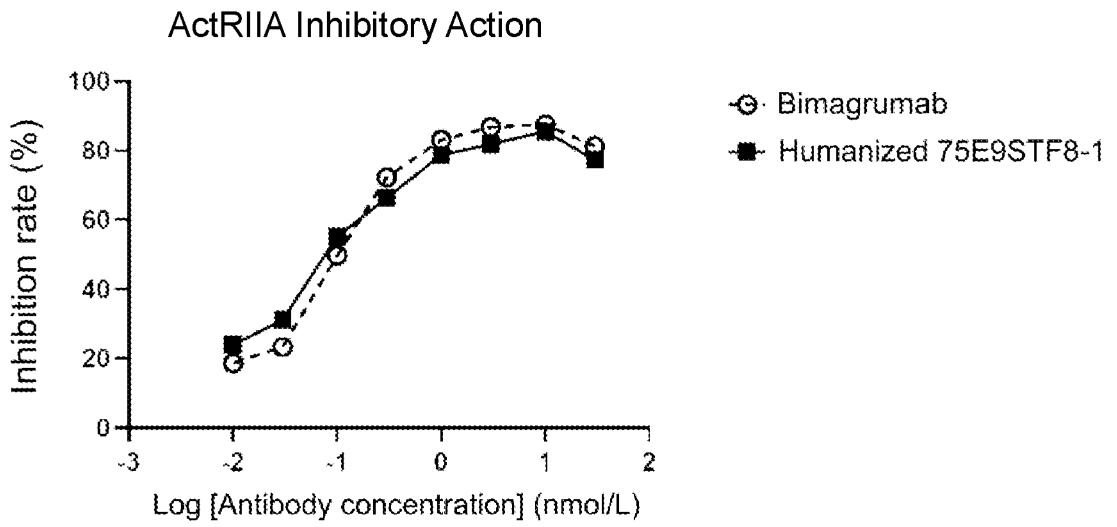
FIG. 1A shows an inhibitory action on myostatin-induced Smad3 phosphorylation in ActRIIA/HEK293 cells (ActRIIA inhibitory action)

Hereinafter, the present invention will be described in detail.

There are five classes of IgG, IgM, IgA, IgD, and IgE in an antibody. The basic structure of an antibody molecule is composed of heavy chains having a molecular weight of 50,000 to 70,000 and light chains having a molecular weight of 20,000 to 30,000 in each of the classes in common. The heavy chain usually consists of a polypeptide chain including approximately 440 amino acids, has a distinctive structure for each of the classes, and is referred to as Ig7, Igp, Iga, Ig6, and IgF corresponding to IgG, IgM, IgA, IgD, and IgE, respectively. Furthermore, four subclasses of IgG1, IgG2, IgG3, and IgG4 are present in IgG, and the heavy chains corresponding thereto are referred to as Igγ1, Igγ2, Igγ3, and Igγ4, respectively. The light chain usually consists of a polypeptide chain including 220 amino acids, two types of which, a type λ and a type κ are known, and are referred to as Igλ and Igκ. In a peptide configuration of the basic structure of antibody molecules, two homologous heavy chains and two homologous light chains are bound by disulfide bonds (S—S bond) and non-covalent bonds, and the molecular weight thereof is 150,000 to 190,000. Two kinds of light chains can be paired with any heavy chain. Each of the antibody molecules typically consists of two identical light chains and two identical heavy chains.

With regard to intrachain S—S bonds, four S—S bonds are present in the heavy chain (five S—S bonds are present in Igμ and Igε chains), two S—S bonds are present in the light chain, one loop is formed every 100 to 110 amino acid residues, and the steric structures are similar in each loop, which is referred to as a structural unit or a domain. The domain located at the N terminal side in both of the heavy chain and the light chain, whose amino acid sequence is not constant even in a case of a sample from the same class (subclass) of the same kind of animals is referred to as a variable region, and respective domains are referred to as a heavy chain variable region (VH) and a light chain variable region (VL). The amino acid sequence on the C terminal side from the variable region is almost constant for each class or subclass, and is referred to as a constant region (each of the domains of the constant region is represented by CH1, CH2, or CH3 from the N terminal side of the heavy chain constant region, and the light chain constant region is represented by CL).

An antigen-binding site of an antibody is composed of VH and VL, and the binding specificities each depend on the amino acid sequence of this site. On the other hand, biological activities such as binding to complements and various Fc receptor expression cells reflect differences in the constant region structures of each class Ig. It is understood that the variability of the variable regions of the light chains and the heavy chains is almost limited to three small hypervariable regions present in both chains and these regions are referred to as complementarity determining regions (CDR: CDR1, CDR2, and CDR3 from the N terminal side). The remaining portion of the variable region is referred to as a framework region (FR) and is relatively constant.

Various antigen-binding fragments including VH and VL of an antibody also have antigen-binding activities, and representative examples of such antigen-binding fragments include a single chain variable region fragment (scFv), Fab, Fab', and F(ab')2. scFv is a monovalent antibody fragment which is composed of VH and VL linked to each other via a linker. Fab is a monovalent antibody fragment which is composed of a light chain and a heavy chain fragment including VH, a CH1 domain, and a portion of a hinge region. Fab' is a monovalent antibody fragment which is composed of a light chain and a heavy chain fragment including VH, a CH1 domain, and a portion of a hinge region, and the portion of the hinge region includes cysteine residues constituting the S—S bond between heavy chains. The F(ab')2 fragment is a divalent antibody fragment in which two Fab' fragments are bound by an S—S bond between heavy chains in the hinge region.

As antibodies derived from camelids (bactrian camels, dromedaries, llamas, and alpacas), antibodies composed only of light chains and CH1 domain-deficient heavy chains (heavy chain antibodies) are known. The variable region of a heavy chain antibody is called a variable domain of a heavy chain of a heavy chain antibody (VHH), and the antigen-binding site of the heavy chain antibody is composed only of VHH. VHH includes three CDRs and the specificity in the binding to an antigen depends on the amino acid sequences of the CDRs.

"VHH" in the present specification also includes humanized forms of VHHs (humanized VHHs), in which a part, the most, or all of the amino acid sequence of FR is substituted with an amino acid sequence derived from a human immunoglobulin molecule. The humanization method is not particularly limited, but for example, a humanized antibody can be produced with reference to International Publication No. 2006/122825, U.S. Pat. Nos. 5,225,539, 6,180,370, and the like.

In the specification, the "multispecific antibody" means an antibody that binds to two or more kinds of different antigens.

In the specification, the "peptide linker" refers to a polypeptide consisting of any one or more amino acid sequences which can be introduced by genetic engineering techniques in order to link variable regions.

Multispecific Antibody of Present Invention

The present invention provides the following multispecific antibody (hereinafter also referred to as "the multispecific antibody of the present invention"):

a multispecific antibody binding to ActRIIA, ActRIIB, and Fn14, the multispecific antibody including (a) a polypeptide including a first VHH and a second VHH, the polypeptide binding to ActRIIA and ActRIIB, and (b) an antibody binding to Fn14 or an antigen-binding fragment thereof, in which the first VHH includes CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 105 of SEQ ID NO: 2, the second VHH includes CDR1 consisting of the amino acid sequence of amino acid numbers 172 to 176 of SEQ ID NO: 2, CDR2 consisting of the amino acid sequence of amino acid numbers 195 to 210 of SEQ ID NO: 2, and CDR3 consisting of the amino acid sequence of amino acid numbers 243 to 251 of SEQ ID NO: 2, and the C terminal of the polypeptide of (a) is linked to the N terminal of a heavy chain variable region of the antibody binding to Fn14 or an antigen-binding fragment thereof via a peptide linker.

In one embodiment of the multispecific antibody of the present invention, the first VHH and the second VHH are humanized VHHs. In one embodiment of the multispecific antibody of the present invention, the first VHH consists of the amino acid sequence of amino acid numbers 1 to 116 of SEQ ID NO: 2 and the second VHH consists of the amino acid sequence of amino acid numbers 142 to 262 of SEQ ID NO: 2.

In the polypeptide of (a) in the multispecific antibody of the present invention, the C terminal of the first VHH may be linked to the N terminal of the second VHH, and the C terminal of the second VHH may be linked to the N terminal of the first VHH. In one embodiment of the multispecific antibody of the present invention, the C terminal of the first VHH is linked to the N terminal of the second VHH.

In the polypeptide of (a) in the multispecific antibody of the present invention, the first VHH and the second VHH may be directly linked or linked via a peptide linker. In one embodiment of the multispecific antibody of the present invention, the first VHH and the second VHH are linked via a peptide linker.

In one embodiment of the multispecific antibody of the present invention, the C terminal of the first VHH is linked to the N terminal of the second VHH via a peptide linker. In one embodiment of the multispecific antibody of the present invention, the first VHH and the second VHH are humanized VHHs, and the C terminal of the first VHH is linked to the N terminal of the second VHH via a peptide linker.

In one embodiment of the multispecific antibody of the present invention, the first VHH consists of the amino acid sequence of amino acid numbers 1 to 116 of SEQ ID NO: 2, the second VHH consists of the amino acid sequence of amino acid numbers 142 to 262 of SEQ ID NO: 2, and the C terminal of the first VHH is linked to the N terminal of the second VHH via a peptide linker.

The length of the peptide linker that links the first VHH and the second VHH is not particularly limited, and can be appropriately selected by those skilled in the art, depending on the purpose. In one embodiment, the first VHH and the second VHH are linked by a peptide linker with 5 amino acids or more, and in one embodiment, the first VHH and the second VHH are linked by a peptide linker with 5 amino acids or more and 35 amino acids or less, 5 amino acids or more and 30 amino acids or less, 5 amino acids or more and 25 amino acids or less, 10 amino acids or more and 25 amino acids or less, or 15 amino acids or more and 25 amino acids or less.

Examples of the peptide linker include the following ones:

Ser

Gly•Ser

Gly•Gly•Ser

Ser•Gly•Gly (SEQ ID NO: 5)
Gly•Gly•Gly•Ser (SEQ ID NO: 6)
Ser•Gly•Gly•Gly (SEQ ID NO: 7)
Gly•Gly•Gly•Gly•Ser (SEQ ID NO: 8)
Ser•Gly•Gly•Gly•Gly (SEQ ID NO: 9)
Gly•Gly•Gly•Gly•Gly•Ser (SEQ ID NO: 10)
Ser•Gly•Gly•Gly•Gly•Gly (SEQ ID NO: 11)
Gly•Gly•Gly•Gly•Gly•Gly•Ser (SEQ ID NO: 12)
Ser•Gly•Gly•Gly•Gly•Gly•Gly (Gly•Gly•Gly•Gly•Ser (SEQ ID NO: 7))$_n$ (Ser•Gly•Gly•Gly•Gly (SEQ ID NO: 8))$_n$

[n is an integer of 1 or more]. In one embodiment, the peptide linker that links the first VHH and the second VHH is (Gly·Gly·Gly·Gly·Ser (SEQ ID NO: 7))$_n$ [n is an integer of 1 to 5], and in one embodiment, the peptide linker that links the first VHH and the second VHH is (Gly·Gly·Gly·Gly·Ser)$_5$ (amino acid numbers 117 to 141 of SEQ ID NO: 2).

In one embodiment of the multispecific antibody of the present invention, the first VHH and the second VHH are humanized VHHs, the C terminal of the first VHH is linked to the N terminal of the second VHH via a peptide linker, and the peptide linker that links the first VHH and the second VHH is (Gly·Gly·Gly·Gly·Ser)$_5$ (amino acid numbers 117 to 141 of SEQ ID NO: 2).

In one embodiment of the multispecific antibody of the present invention, the polypeptide of (a) consists of the amino acid sequence of amino acid numbers 1 to 262 of SEQ ID NO: 2.

In one embodiment of the multispecific antibody of the present invention, the antibody binding to Fn14 or an antigen-binding fragment thereof includes a heavy chain variable region including CDR1 consisting of the amino acid sequence of amino acid numbers 303 to 307 of SEQ ID NO: 2, CDR2 consisting of the amino acid sequence of amino acid numbers 322 to 338 of SEQ ID NO: 2, and CDR3 consisting of the amino acid sequence of amino acid numbers 371 to 379 of SEQ ID NO: 2, and a light chain variable region including CDR1 consisting of the amino acid sequence of amino acid numbers 24 to 34 of SEQ ID NO: 4, CDR2 consisting of the amino acid sequence of amino acid numbers 50 to 56 of SEQ ID NO: 4, and CDR3 consisting of the amino acid sequence of amino acid numbers 89 to 97 of SEQ ID NO: 4.

In one embodiment of the multispecific antibody of the present invention, the antibody binding to Fn14 or an antigen-binding fragment thereof includes a heavy chain variable region consisting of the amino acid sequence of amino acid numbers 273 to 390 of SEQ ID NO: 2 and a light chain variable region consisting of the amino acid sequence of amino acid numbers 1 to 108 of SEQ ID NO: 4.

In one embodiment of the multispecific antibody of the present invention, the antigen-binding fragment of an antibody binding to Fn14 is an antigen-binding fragment which is scFv, Fab, Fab', or F(ab')2.

Any subclass of a constant region (for example, a constant region of Igγ1, Igγ2, Igγ3, or Igγ4 as a heavy chain constant region, and Igλ or Igκ as a light chain) can be selected as the constant region in the antibody binding to Fn14. In one embodiment, the antibody binding to Fn14 includes a human Igγ1 constant region as the heavy chain constant region and a human Igκ constant region as the light chain constant region.

The residue number related to the introduction of amino acid mutations in the constant region of the antibody used herein can be defined according to the EU index (Kabat et al., 1991, Sequences of Proteins of Immunological Interest, 5th Ed., United States Public Health Service, National Institute of Health, Bethesda). L234A is a substitution of leucine at the amino acid 234 position with alanine in the human Igγ1 constant region according to the EU index of Kabat et al. L235A is a substitution of leucine at the amino acid 235 position with alanine in the human Igγ1 constant region according to the EU index of Kabat et al. M252Y is a substitution of methionine at the amino acid 252 position with tyrosine in the human Igγ1 constant region according to the EU index of Kabat et al. S254T is a substitution of serine at the amino acid 254 position with threonine in the human Igγ1 constant region according to the EU index of Kabat et al. T256E is a substitution of threonine at the amino acid 256 position with glutamic acid in the human Igγ1 constant region according to the EU index of Kabat et al.

In one embodiment of the multispecific antibody of the present invention, the multispecific antibody includes an antibody binding to Fn14, and the antibody binding to Fn14 includes a heavy chain constant region having amino acid mutations of L234A, L235A, M252Y, S254T, and T256E. Examples of the constant regions having amino acid mutations of L234A, L235A, M252Y, S254T, and T256E include a human Igγ1 constant region consisting of the amino acid sequence of amino acid numbers 391 to 720 of SEQ ID NO: 2.

In one embodiment of the multispecific antibody of the present invention, the multispecific antibody includes an antibody binding to Fn14, and the antibody binding to Fn14 includes a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E, and a light chain including a light chain variable region consisting of the amino acid sequence of amino acid numbers 1 to 108 of SEQ ID NO: 4 and a light chain constant region.

In one embodiment of the multispecific antibody of the present invention, the multispecific antibody includes an antibody binding to Fn14, and the antibody binding to Fn14 includes a heavy chain consisting of the amino acid sequence set forth in amino acid numbers 273 to 720 of SEQ ID NO: 2 and a light chain consisting of the amino acid sequence set forth in SEQ ID NO: 4.

In the multispecific antibody of the present invention, the C terminal of the polypeptide of (a) is linked to the N terminal of a heavy chain variable region of the antibody binding to Fn14 or an antigen-binding fragment thereof via a peptide linker. The length of the peptide linker to be used is not particularly limited, and can be appropriately selected by those skilled in the art, depending on the purpose. In one embodiment, the polypeptide of (a) and the antibody binding to Fn14 or an antigen-binding fragment thereof are linked by a peptide linker with 5 amino acids or more, and in one embodiment, the polypeptide of (a) and the antibody binding to Fn14 or an antigen-binding fragment thereof is linked by a peptide linker with 5 amino acids or more and 35 amino acids or less, 5 amino acids or more and 30 amino acids or less, 5 amino acids or more and 25 amino acids or less, 5 amino acids or more and 20 amino acids or less, or 10 amino acids or more and 20 amino acids or less.

Examples of the peptide linker include the following ones:

```
Ser

Gly•Ser

Gly•Gly•Ser

Ser•Gly•Gly

                                        (SEQ ID NO: 5)
Gly•Gly•Gly•Ser

                                        (SEQ ID NO: 6)
Ser•Gly•Gly•Gly

                                        (SEQ ID NO: 7)
Gly•Gly•Gly•Gly•Ser

                                        (SEQ ID NO: 8)
Ser•Gly•Gly•Gly•Gly

                                        (SEQ ID NO: 9)
Gly•Gly•Gly•Gly•Gly•Ser

                                       (SEQ ID NO: 10)
Ser•Gly•Gly•Gly•Gly•Gly

                                       (SEQ ID NO: 11)
Gly•Gly•Gly•Gly•Gly•Gly•Ser

                                       (SEQ ID NO: 12)
Ser•Gly•Gly•Gly•Gly•Gly•Gly

(Gly•Gly•Gly•Gly•Ser (SEQ ID NO: 7))n

(Ser Gly•Gly•Gly•Gly (SEQ ID NO: 8))n
```

[n is an integer of 1 or more]. In one embodiment, the peptide linker that links the polypeptide of (a) and the antibody binding to Fn14 or an antigen-binding fragment thereof is (Gly·Gly·Gly·Gly·Ser (SEQ ID NO: 7))$_n$ [n is an integer of 1 to 5], and in one embodiment, the peptide linker that links the polypeptide of (a) and the antibody binding to Fn14 or an antigen-binding fragment thereof is (Gly·Gly·Gly·Gly·Ser)$_2$ (amino acid numbers 263 to 272 of SEQ ID NO: 2).

In the multispecific antibody of the present invention, the peptide linker that links the first VHH and the second VHH and the peptide linker that links the polypeptide of (a) and the antibody binding to Fn14 or an antigen-binding fragment thereof are the same peptide linker or different peptide linkers.

In one embodiment, the multispecific antibody of the present invention is the following multispecific antibody:

a multispecific antibody binding to ActRIIA, ActRIIB, and Fn14, the multispecific antibody including:

(a) a polypeptide including a first VHH and a second VHH, the polypeptide binding to ActRIIA and ActRIIB, and (b) an antibody binding to Fn14 or an antigen-binding fragment thereof, in which the first VHH consists of the amino acid sequence of amino acid numbers 1 to 116 of SEQ ID NO: 2 and the second VHH consists of the amino acid sequence of amino acid numbers 142 to 262 of SEQ ID NO: 2, the antibody binding to Fn14 or an antigen-binding fragment thereof includes a heavy chain variable region consisting of the amino acid sequence of amino acid numbers 273 to 390 of SEQ ID NO: 2 and a light chain variable region consisting of the amino acid sequence of amino acid numbers 1 to 108 of SEQ ID NO: 4, and the C terminal of the polypeptide of (a) is linked to the N terminal of a heavy chain variable region of the antibody binding to Fn14 or an antigen-binding fragment thereof via a peptide linker.

In one embodiment, the multispecific antibody of the present invention is the following multispecific antibody:

a multispecific antibody binding to ActRIIA, ActRIIB, and Fn14, the multispecific antibody including:

(a) a polypeptide including a first VHH and a second VHH, the polypeptide binding to ActRIIA and ActRIIB, and (b) an antibody binding to Fn14, in which the first VHH consists of the amino acid sequence of amino acid numbers 1 to 116 of SEQ ID NO: 2 and the second VHH consists of the amino acid sequence of amino acid numbers 142 to 262 of SEQ ID NO: 2, the antibody binding to Fn14 includes a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E, and a light chain including a light chain variable region consisting of the amino acid sequence of amino acid numbers 1 to 108 of SEQ ID NO: 4 and a light chain constant region, and the C terminal of the polypeptide of (a) is linked to the N terminal of a heavy chain variable region of an antibody binding to Fn14 via a peptide linker.

In one embodiment, the multispecific antibody of the present invention is the following multispecific antibody:

a multispecific antibody binding to ActRIIA, ActRIIB, and Fn14, the multispecific antibody including:

(a) a polypeptide including a first VHH and a second VHH, the polypeptide binding to ActRIIA and ActRIIB, and (b) an antibody binding to Fn14, in which the first VHH consists of the amino acid sequence of amino acid numbers 1 to 116 of SEQ ID NO: 2 and the second VHH consists of the amino acid sequence of amino acid numbers 142 to 262 of SEQ ID NO: 2, the antibody binding to Fn14 includes a heavy chain consisting of the amino acid sequence set forth in amino acid numbers 273 to 720 of SEQ ID NO: 2 and a light chain consisting of the amino acid sequence set forth in SEQ ID NO: 4, and the C terminal of the polypeptide of (a) is linked to the N terminal of a heavy chain variable region of an antibody binding to Fn14 via a peptide linker.

In one embodiment, the multispecific antibody of the present invention is the following multispecific antibody:

a multispecific antibody binding to ActRIIA, ActRIIB, and Fn14, the multispecific antibody including:

(a) a polypeptide including a first VHH and a second VHH, the polypeptide binding to ActRIIA and ActRIIB, and (b) an antibody binding to Fn14 or an antigen-binding fragment thereof, in which the first VHH consists of the amino acid sequence of amino acid numbers 1 to 116 of SEQ ID NO: 2, the second VHH consists of the amino acid sequence of amino acid numbers 142 to 262 of SEQ ID NO: 2, and the C terminal of the first VHH is linked to the N terminal of the second VHH via a peptide linker, the antibody binding to Fn14 or an antigen-binding fragment thereof includes a heavy chain variable region consisting of the amino acid sequence of amino acid numbers 273 to 390 of SEQ ID NO: 2 and a light chain variable region consisting of the amino acid sequence of amino acid numbers 1 to 108 of SEQ ID NO: 4, and the C terminal of the polypeptide of (a) is linked to the N terminal of a heavy chain variable region of the antibody binding to Fn14 or an antigen-binding fragment thereof via a peptide linker.

In one embodiment, the multispecific antibody of the present invention is the following multispecific antibody:

a multispecific antibody binding to ActRIIA, ActRIIB, and Fn14, the multispecific antibody including:

(a) a polypeptide including a first VHH and a second VHH, the polypeptide binding to ActRIIA and ActRIIB, and (b) an antibody binding to Fn14, in which the first VHH consists of the amino acid sequence of amino acid numbers 1 to 116 of SEQ ID NO: 2, the second VHH consists of the amino acid sequence of amino acid numbers 142 to 262 of SEQ ID NO: 2, and the C terminal of the first VHH is linked to the N terminal of the second VHH via a peptide linker, the antibody binding to Fn14 or an antigen-binding fragment thereof includes a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E, and a light chain including a light chain variable region consisting of the amino acid sequence of amino acid numbers 1 to 108 of SEQ ID NO: 4 and a light chain constant region, and the C terminal of the polypeptide of (a) is linked to the N terminal of a heavy chain variable region of an antibody binding to Fn14 via a peptide linker.

In one embodiment, the multispecific antibody of the present invention is the following multispecific antibody:

a multispecific antibody binding to ActRIIA, ActRIIB, and Fn14, the multispecific antibody including:

(a) a polypeptide including a first VHH and a second VHH, the polypeptide binding to ActRIIA and ActRIIB, and (b) an antibody binding to Fn14, in which the first VHH consists of the amino acid sequence of amino acid numbers 1 to 116 of SEQ ID NO: 2, the second VHH consists of the amino acid sequence of amino acid numbers 142 to 262 of SEQ ID NO: 2, and the C terminal of the first VHH is linked to the N terminal of the second VHH via a peptide linker, the antibody binding to Fn14 includes a heavy chain consisting of the amino acid sequence set forth in amino acid numbers 273 to 720 of SEQ ID NO: 2 and a light chain consisting of the amino acid sequence set forth in SEQ ID NO: 4, and the C terminal of the polypeptide of (a) is linked to the N terminal of a heavy chain variable region of an antibody binding to Fn14 via a peptide linker.

In one embodiment, the multispecific antibody of the present invention is the following multispecific antibody:

a multispecific antibody binding to ActRIIA, ActRIIB, and Fn14, the multispecific antibody including:

(a) a polypeptide including a first VHH and a second VHH, the polypeptide binding to ActRIIA and ActRIIB, and (b) an antibody binding to Fn14 or an antigen-binding fragment thereof, in which the polypeptide of (a) consists of the amino acid sequence of amino acid numbers 1 to 262 of SEQ ID NO: 2, the antibody binding to Fn14 or an antigen-binding fragment thereof includes a heavy chain variable region consisting of the amino acid sequence of amino acid numbers 273 to 390 of SEQ ID NO: 2 and a light chain variable region consisting of the amino acid sequence of amino acid numbers 1 to 108 of SEQ ID NO: 4, and the C terminal of the polypeptide of (a) is linked to the N terminal of a heavy chain variable region of the antibody binding to Fn14 or an antigen-binding fragment thereof via a peptide linker.

In one embodiment, the multispecific antibody of the present invention is the following multispecific antibody:

a multispecific antibody binding to ActRIIA, ActRIIB, and Fn14, the multispecific antibody including:

(a) a polypeptide including a first VHH and a second VHH, the polypeptide binding to ActRIIA and ActRIIB, and (b) an antibody binding to Fn14, in which the polypeptide of (a) consists of the amino acid sequence of amino acid numbers 1 to 262 of SEQ ID NO: 2, the antibody binding to Fn14 includes a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E, and a light chain including a light chain variable region consisting of the amino acid sequence of amino acid numbers 1 to 108 of SEQ ID NO: 4 and a light chain constant region, and the C terminal of the polypeptide of (a) is linked to the N terminal of a heavy chain variable region of an antibody binding to Fn14 via a peptide linker.

In one embodiment, the multispecific antibody of the present invention is the following multispecific antibody:

a multispecific antibody binding to ActRIIA, ActRIIB, and Fn14, the multispecific antibody including:

(a) a polypeptide including a first VHH and a second VHH, the polypeptide binding to ActRIIA and ActRIIB, and (b) an antibody binding to Fn14, in which the polypeptide of (a) consists of the amino acid sequence of amino acid numbers 1 to 262 of SEQ ID NO: 2, the antibody binding to Fn14 includes a heavy chain consisting of the amino acid sequence set forth in amino acid numbers 273 to 720 of SEQ ID NO: 2 and a light chain consisting of the amino acid sequence set forth in SEQ ID NO: 4, and the C terminal of the polypeptide of (a) is linked to the N terminal of a heavy chain variable region of an antibody binding to Fn14 via a peptide linker.

In one embodiment, the multispecific antibody of the present invention includes a polypeptide consisting of the amino acid sequence of SEQ ID NO: 2 and a light chain consisting of the amino acid sequence of SEQ ID NO: 4.

It is known that in a case where an antibody is expressed in cells, the antibody is modified after translation. Examples of the post-translational modification include lysine deletion at the C terminal of the heavy chain by a carboxypeptidase, modification of glutamine or glutamic acid at the N terminal of the heavy chain and the light chain to pyroglutamic acid by pyroglutamylation, glycosylation, oxidation, deamidation, and glycation, and it is known that such post-translational modifications occur in various antibodies (Liu H et al., J Pharm Sci. 2008, Vol. 97, p. 2426-2447).

The multispecific antibody of the present invention also includes a post-translationally modified multispecific antibody. In one embodiment, the multispecific antibody of the present invention is a multispecific antibody with pyroglutamylation at the N terminal of the polypeptide of (a) and/or lysine deletion at the heavy chain C terminal of the antibody that binding to Fn14 of the above-described multispecific antibody of the present invention. It is known in the field that such post-translational modification due to pyroglutamylation at the N terminal or lysine deletion at the C terminal does not have any influence on the activity of the antibody (Lyubarskaya Y et al., Anal Biochem. 2006, Vol. 348, p. 24-39).

Any of those skilled in the art can manufacture a fused product from in which the multispecific antibody of the present invention is fused with another peptide or protein, or can also prepare a modified product to which a modifier is bound, based on the present invention, and these forms of multispecific antibodies are also included in the multispecific antibody of the present invention. Other peptides or proteins used for the fusion are not particularly limited as long as the fused product binds to ActRIIA, ActRIIB, and Fn14, and examples thereof include human serum albumin, various tag peptides, artificial helix motif peptides, maltose-binding proteins, glutathione S transferase, various toxins, and other peptides or proteins capable of promoting multimerization. The modifier used for the modification is not particularly limited as long as the modified product binds to ActRIIA, ActRIIB, and Fn14, and examples thereof include polyethylene glycol, sugar chains, phospholipids, liposomes, and low-molecular compounds. In one embodiment, the modifier used to modify the multispecific antibody of the present invention is polyethylene glycol.

The multispecific antibody of the present invention includes a first VHH and a second VHH, binding to ActRIIA and ActRIIB, and an antibody binding to Fn14 or an antigen-binding fragment. The multispecific antibody of the present invention binds to ActRIIA, ActRIIB, and Fn14. Whether or not the multispecific antibody binds to ActRIIA, ActRIIB, or Fn14 can be confirmed using a known binding activity measurement method. Examples of the binding activity measurement method include an Enzyme-Linked immunnoSorbent Assay (ELISA). In a case of using the ELISA, for example, an ActRIIA, ActRIIB, or Fn14 protein is immobilized on an ELISA plate and a test antibody is added thereto to be reacted, and after the reaction, a secondary antibody such as an anti-IgG antibody, labeled with an enzyme such as horseradish peroxidase (HRP), is reacted. After the reaction, washing is performed, and then it is possible to confirm whether the test antibody binds to ActRIIA, ActRIIB, or Fn14 by identifying binding of the secondary antibody through an activity measurement using a reagent detecting the activity (for example, in a case of HRP labeling, TMB Microwell Peroxidase Substrate (Kirkegaard & Perry Laboratories, Inc., 50-76-03)). As a specific measurement method, the method described in Example 5 below can be used.

Examples of the multispecific antibody of the present invention also include multispecific antibodies that bind to not only human ActRIIA, human ActRIIB, and human Fn14, but also ActRIIA, ActRIIB, and Fn14 derived from other animals (mice, monkeys, and the like). In one embodiment, the multispecific antibody of the present invention binds to human ActRIIA, human ActRIIB, and human Fn14.

The multispecific antibody of the present invention can be readily manufactured by those skilled in the art, based on the sequence information of the multispecific antibody of the present invention disclosed in the present specification, using a method known in the art. The multispecific antibody of the present invention is not particularly limited, but can be produced, for example, according to the method described in <Method for Producing Multispecific Antibody of Present Invention> below.

The multispecific antibody of the present invention can be further purified as necessary, formulated according to a standard method, and used for prevention or treatment of amyotrophic diseases such as inclusion body myositis.

Polynucleotide of Present Invention

The present invention also provides the following polynucleotides of (1) to (4) (also referred to as "the polynucleotide of the present invention"):

(1) a polynucleotide including a nucleotide sequence encoding the polypeptide including the first VHH and the second VHH of the multispecific antibody of the present invention (the polypeptide of (a)), (2) a polynucleotide including a nucleotide sequence encoding a heavy chain variable region of the antibody binding to Fn14 or an antigen-binding fragment thereof in the multispecific antibody of the present invention, (3) a polynucleotide including a nucleotide sequence encoding the light chain variable region of the antibody binding to Fn14 or an antigen-binding fragment thereof in the multispecific antibody of the present invention, and (4) a polynucleotide including a nucleotide sequence encoding the polypeptide including the first VHH and the second VHH (the polypeptide of (a)) and a polypeptide including a heavy chain variable region of the antibody binding to Fn14 or an antigen-binding fragment thereof in the multispecific antibody of the present invention.

In one embodiment, the polynucleotide of (1) is a polynucleotide including a nucleotide sequence encoding a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2. In one embodiment, the polynucleotide of (1) is a polynucleotide including a nucleotide sequence encoding a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, in which the C terminal of the first VHH is linked to the N terminal of the second VHH via a peptide linker. In one embodiment, the polynucleotide of (1) is a polynucleotide including a nucleotide sequence encoding a polypeptide consisting of the amino acid sequence of amino acid numbers 1 to 262 of SEQ ID NO: 2.

In one embodiment, the polynucleotide of (2) is a polynucleotide including a nucleotide sequence encoding a heavy chain variable region consisting of the amino acid sequence of amino acid numbers 273 to 390 of SEQ ID NO: 2. In one embodiment, the polynucleotide of (2) is polynucleotide including a nucleotide sequence encoding a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E. In one embodiment, the polynucleotide of (2) is a polynucleotide including a nucleotide sequence encoding a heavy chain consisting of the amino acid sequence set forth in amino acid numbers 273 to 720 of SEQ ID NO: 2.

In one embodiment, the polynucleotide of (3) is a polynucleotide including a nucleotide sequence encoding a light chain variable region consisting of the amino acid sequence of amino acid numbers 1 to 108 of SEQ ID NO: 4. In one embodiment, the polynucleotide of (3) is a polynucleotide including a nucleotide sequence encoding a light chain including a light chain variable region consisting of the amino acid sequence of amino acid numbers 1 to 108 of SEQ ID NO: 4 and a light chain constant region. In one embodiment, the polynucleotide of (3) is a polynucleotide including a nucleotide sequence encoding a light chain consisting of the amino acid sequence set forth in SEQ ID NO: 4.

In one embodiment, the polynucleotide of (4) is a polynucleotide including a nucleotide sequence encoding a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, and a polypeptide including a heavy chain variable region of an antibody binding to Fn14 or an antigen-binding fragment thereof. In one embodiment, the polynucleotide of (4) is a polynucleotide including a nucleotide sequence encoding a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, in which the C terminal of the first VHH is linked to the N terminal of the second VHH via a peptide linker, and a polypeptide including a heavy chain variable region of an antibody binding to Fn14 or an antigen-binding fragment thereof. In one embodiment, the polynucleotide of (4) is a polynucleotide including a nucleotide sequence encoding a polypeptide including an amino acid sequence of amino acid numbers 1 to 262 of SEQ ID NO: 2 and a polypeptide including a heavy chain variable region of an antibody binding to Fn14 or an antigen-binding fragment thereof.

In one embodiment, the polynucleotide of (4) is a polynucleotide including a nucleotide sequence encoding a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, and a polypeptide including a heavy chain variable region consisting of the amino acid sequence of amino acid numbers 273 to 390 of SEQ ID NO: 2. In one embodiment, the polynucleotide of (4) is a polynucleotide including a nucleotide sequence encoding a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, in which the C terminal of the first VHH is linked to the N terminal of the second VHH via a peptide linker, and a polypeptide including a heavy chain variable region consisting of the amino acid sequence of amino acid numbers 273 to 390 of SEQ ID NO: 2. In one embodiment, the polynucleotide of (4) is a polynucleotide including a nucleotide sequence encoding a polypeptide consisting of the amino acid sequence of amino acid numbers 1 to 262 of SEQ ID NO: 2 and a polypeptide including a heavy chain variable region consisting of the amino acid sequence of amino acid numbers 273 to 390 of SEQ ID NO: 2.

In one embodiment, the polynucleotide of (4) is a polynucleotide including a nucleotide sequence encoding a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, and a polypeptide including a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E. In one embodiment, the polynucleotide of (4) is a polynucleotide including a nucleotide sequence encoding a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, in which the C terminal of the first VHH is linked to the N terminal of the second VHH via a peptide linker, and a polypeptide including a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E. In one embodiment, the polynucleotide of (4) is a polynucleotide including a nucleotide sequence encoding a polypeptide consisting of the amino acid sequence of amino acid numbers 1 to 262 of SEQ ID NO: 2, and a polypeptide including a heaving chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E.

In one embodiment, the polynucleotide of (4) is a polynucleotide including a nucleotide sequence encoding a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, and a polypeptide including a heavy chain consisting of the amino acid sequence set forth in amino acid numbers 273 to 720 of SEQ ID NO: 2. In one embodiment, the polynucleotide of (4) is a polynucleotide including a nucleotide sequence encoding a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, in which the C terminal of the first VHH is linked to the N terminal of the second VHH via a peptide linker, and a polypeptide including a heavy chain consisting of the amino acid sequence set forth in amino acid numbers 273 to 720 of SEQ ID NO: 2. In one embodiment, the polynucleotide of (4) is a polynucleotide including a nucleotide sequence encoding a polypeptide consisting of the amino acid sequence of amino acid numbers 1 to 262 of SEQ ID NO: 2 and a polypeptide including a heavy chain consisting of the amino acid sequence set forth in amino acid numbers 273 to 720 of SEQ ID NO: 2.

In one embodiment, the polynucleotide of (4) is a polynucleotide including a nucleotide sequence encoding a polypeptide consisting of the amino acid sequence of SEQ ID NO: 2.

Based on the nucleotide sequence, the polynucleotide of the present invention can be readily manufactured by those skilled in the art by using methods known in the art. For example, the polynucleotide of the present invention can be synthesized by using gene synthesis methods known in the art. As such a gene synthesis method, various methods known to those skilled in the art such as a method for synthesizing an antibody gene described in International Publication No. 90/07861 can be used.

Expression Vector of Present Invention

The present invention also provides an expression vector including the polynucleotide of the present invention (also referred to as "the expression vector of the present invention"). In one embodiment, the expression vector of the present invention includes any of the polynucleotides of (1) to (4) described in the section of <Polynucleotides of Present Invention>. Specific examples of an embodiment of the polynucleotide included in the expression vector of the present invention include those described for the polynucleotides of (1) to (4) described in the section of <Polynucleotide of Present Invention>.

In one embodiment, the expression vector of the present invention includes (i) a polynucleotide including a nucleotide sequence encoding the light chain variable region of the antibody binding to Fn14 or an antigen-binding fragment thereof in the multispecific antibody of the present invention and/or (ii) a polynucleotide including a nucleotide sequence encoding the polypeptide including the first VHH and the second VHH (the polypeptide of (a)) and the polypeptide including the heavy chain variable region of the antibody binding to Fn14 or an antigen-binding fragment thereof in the multispecific antibody of the present invention.

Specific examples of an embodiment of the polynucleotides of (i) and (ii) included in the expression vector of the present invention include those described for the polynucleotides of (3) and (4) described in the section of <Polynucleotide of Present Invention>.

In one embodiment, the expression vector of the present invention is an expression vector including a polynucleotide including a nucleotide sequence encoding a polypeptide consisting of the amino acid sequence of SEQ ID NO: 2, an expression vector including a polynucleotide including a nucleotide sequence encoding a light chain consisting of the amino acid sequence of SEQ ID NO: 4, or an expression vector including a polynucleotide including a nucleotide sequence encoding a polypeptide consisting of the amino acid sequence of SEQ ID NO: 2 and a polynucleotide including a nucleotide sequence encoding a light chain consisting of the amino acid sequence of SEQ ID NO: 4.

The expression vector used to express the polynucleotide of the present invention is not particularly limited as long as it can express a polynucleotide including a nucleotide sequence encoding the first VHH of the multispecific antibody of the present invention and a polynucleotide including a nucleotide sequence encoding the second VHH of the multispecific antibody in various host cells of eukaryotic cells (for example, animal cells, insect cells, plant cells, and yeasts) and/or prokaryotic cells (for example, *Escherichia coli*), and thus, produce a polypeptide encoded therewith. Examples of such an expression vector include plasmid vectors and viral vectors (for example, adenovirus and retrovirus), and for example, plasmid vectors such as pEE6.4 and pEE12.4 can be used. An antibody gene can also be expressed by introducing a variable region gene segment into an expression vector already having a human Ig constant region gene such as AG-γ1 and AG-κ (seem for example, International Publication No. 94/20632).

The expression vector of the present invention may include a promoter operably linked to the polynucleotide of the present invention. Examples of the promoter for expressing the polynucleotide of the present invention in an animal cell include a virus-derived promoter such as CMV, RSV, and SV40, an actin promoter, an elongation factor (EF) 1α promoter, and a heat shock promoter. Examples of the promoter for expressing a polynucleotide by bacteria (for example, *Escherichia*) include a trp promoter, a lac promoter, a λPL promoter, and a tac promoter. In addition, examples of the promoter for expressing a polynucleotide by a yeast include a GAL1 promoter, a GAL10 promoter, a PH05 promoter, a PGK promoter, a GAP promoter, and an ADH promoter.

In a case where an animal cell, an insect cell, or a yeast is used as a host cell, the expression vector of the present invention can include an initiation codon and a termination codon. In this case, the expression vector of the present invention may include an enhancer sequence, an untranslated region on the 5' side and the 3' side of a gene encoding the multispecific antibody of the present invention or the heavy chain variable region or light chain variable region thereof, a secretory signal sequence, a splicing junction, a polyadenylation site, or a replicable unit. In a case where *Escherichia coli* is used as the host cell, the expression vector of the present invention may include an initiation codon, a termination codon, a terminator region, and a replicable unit. In this case, the expression vector of the present invention may include a selection marker (for example, tetracycline resistant genes, ampicillin resistant genes, kanamycin resistant genes, neomycin resistant genes, or dihydrofolate reductase genes) which is generally used according to the purpose.

Transfected Host Cell of Present Invention

The present invention also provides a host cell transfected with the expression vector of the present invention (also referred to as "the transfected host cell of the present invention"). In one embodiment, the host cell of the present invention is a host cell transfected with an expression vector including any of the polynucleotides of (1) to (4) described in the section of <Polynucleotide of Present Invention>. Specific examples of an embodiment of the polynucleotide included in the expression vector include those described for the polynucleotides of (1) to (4) described in the section of <Polynucleotide of Present Invention>.

In one embodiment, the host cell of the present invention is a host cell transfected with an expression vector including the following polynucleotide of (i) and/or (ii), or an expression vector including the following polynucleotide of (i) and/or an expression vector including the following polynucleotide of (ii):

(i) a polynucleotide including a nucleotide sequence encoding the light chain variable region of the antibody binding to Fn14 or an antigen-binding fragment thereof in the multispecific antibody of the present invention;

(ii) a polynucleotide including a nucleotide sequence encoding the polypeptide including the first VHH and the second VHH (the polypeptide of (a)) and a polypeptide including a heavy chain variable region of the antibody binding to Fn14 or an antigen-binding fragment thereof in the multispecific antibody of the present invention.

Specific examples of the embodiment of the polynucleotides of (i) and (ii) in the host cell of the present invention include those described for the polynucleotides of (3) and (4) described in the section of <Polynucleotide of Present Invention>.

In one embodiment, the transfected host cell of the present invention includes a host cell transfected with an expression vector of the present invention, selected from the group consisting of the following (A) to (D):

(A) a host cell transfected with an expression vector including a polynucleotide including a nucleotide sequence encoding a polypeptide consisting of the amino acid sequence of SEQ ID NO: 2 and a polynucleotide including a nucleotide sequence encoding a light chain consisting of the amino acid sequence of SEQ ID NO: 4;

(B) a host cell transfected with an expression vector including a polynucleotide including a nucleotide sequence encoding a polypeptide consisting of the amino acid sequence of SEQ ID NO: 2 and an expression vector including a polynucleotide including a nucleotide sequence encoding a light chain consisting of the amino acid sequence of SEQ ID NO: 4;

(C) a host cell transfected with an expression vector including a polynucleotide including a nucleotide sequence encoding a polypeptide consisting of the amino acid sequence of SEQ ID NO: 2; and (D) a host cell transfected with an expression vector including a polynucleotide including a nucleotide sequence encoding a light chain consisting of the amino acid sequence of SEQ ID NO: 4.

The transfected host cell is not particularly limited as long as the host cell is appropriate for an expression vector to be used, transfected with the expression vector, and can express the multispecific antibody. Examples of the transfected host cell include various cells such as natural cells or artificially established cells which are generally used in the field of the present invention (for example, animal cells (for example, CHO-K1SV cells), insect cells (for example, Sf9), bacteria (for example, *Escherichia*), yeast (for example, *Saccharomyces* or *Pichia*) and the like). For example, cultured cells such as CHO cells (CHO-K1SV cells and CHO-DG44 cells), 293 cells, and NS0 cells can be used.

A method for transfecting the host cell is not particularly limited, and for example, a calcium phosphate method or an electroporation method can be used.

Method for Producing Multispecific Antibody of Present Invention

The present invention also provides a method for producing a multispecific antibody binding to ActRIIA, ActRIIB, and Fn14, the method including a step of culturing the transfected host cell of the present invention to express the multispecific antibody (also referred to as "the production method of the present invention").

In one embodiment, the production method of the present invention includes a step of culturing a host cell transfected with an expression vector including the following polynucleotides of (i) and (ii), or an expression vector including the following polynucleotide of (i) and an expression vector including the following polynucleotide of (ii) to express the multispecific antibody:

(i) a polynucleotide including a nucleotide sequence encoding the polypeptide including the light chain variable region of the antibody binding to Fn14 or an antigen-binding fragment thereof in the multispecific antibody of the present invention;

(ii) a polynucleotide including a nucleotide sequence encoding the polypeptide including the first VHH and the second VHH (the polypeptide of (a)) and a polypeptide including a heavy chain variable region of the antibody binding to Fn14 or an antigen-binding fragment thereof in the multispecific antibody of the present invention.

Specific examples of the embodiment of the polynucleotides of (i) and (ii) in the production method of the present invention include those described for the polynucleotides of (3) and (4) described in the section of <Polynucleotide of Present Invention>.

In one embodiment, the production method of the present invention is a method for producing a multispecific antibody binding to ActRIIA, ActRIIB, and Fn14, the method including a step of culturing a host cell selected from the group consisting of the following (A) to (C) to express the multispecific antibody:

(A) a host cell transfected with an expression vector including a polynucleotide including a nucleotide sequence encoding a polypeptide consisting of the amino acid sequence of SEQ ID NO: 2 and a polynucleotide including a nucleotide sequence encoding a light chain consisting of the amino acid sequence of SEQ ID NO: 4;

(B) a host cell transfected with an expression vector including a polynucleotide including a nucleotide sequence encoding a polypeptide consisting of the amino acid sequence of SEQ ID NO: 2 and an expression vector including a polynucleotide including a nucleotide sequence encoding a light chain consisting of the amino acid sequence of SEQ ID NO: 4;

(C) a host cell transfected with an expression vector including a polynucleotide including a nucleotide sequence encoding a polypeptide consisting of the amino acid sequence of SEQ ID NO: 2; and a host cell transfected with an expression vector including a polynucleotide including a nucleotide sequence encoding a light chain consisting of the amino acid sequence of SEQ ID NO: 4.

The transfected host cell can be cultured by a known method. The culture conditions, for example, the temperature, the pH of culture medium, and the culture time are appropriately selected. In a case where the host cell is an animal cell, examples of the culture medium include MEM culture medium supplemented with approximately 5% to 20% of fetal bovine serum (Eagle H, Science. 1959, Vol. 130, p. 432-437), DMEM culture medium (Dulbecco R and Freeman G, Virology. 1959, Vol. 8, p. 396-397), RPMI1640 culture medium (Moore G E et al., JAMA. 1967, Vol. 199, p. 519-524), and 199 culture medium (Morgan J F et al., Proc Soc Exp Biol Med. 1950, Vol. 73, p. 1-8). The pH of the culture medium is preferably approximately 6 to 8, and the culturing is generally performed at approximately 30° C. to 40° C. for approximately 15 to 336 hours under optional ventilation or stirring. In a case where the host cell is an insect cell, as the culture medium, for example, Grace's culture medium (Smith G E et al., Proc Natl Acad Sci USA., 1985, Vol. 82, p. 8404-8408) supplemented with fetal bovine serum can be used. The pH of the culture medium is preferably approximately 5 to 8, and the culturing is generally performed at approximately 20° C. to 40° C. for approximately 15 hours to 100 hours under optional ventilation or stirring. In a case where the host cell is *Escherichia coli* or yeast, as the culture medium, for example, liquid culture medium supplemented with a source of nutrients is appropriate. The nutrient culture medium preferably includes a carbon source, an inorganic nitrogen source, or an organic nitrogen source necessary for the growth of the transfected host cell. Examples of the carbon source include glucose, dextran, soluble starch, and sucrose and examples of the inorganic nitrogen source or the organic nitrogen source include ammonium salts, nitrate salts, amino acids, corn steep liquor, peptone, casein, meat extract, soybean meal, and potato extract. Other nutrients (for example, inorganic salts (for example, calcium chloride, sodium dihydrogen phosphate, and magnesium chloride), vitamins), and antibiotics (for example, tetracycline, neomycin, ampicillin, and kanamycin) may be included as desired. The pH of the culture medium is preferably approximately 5 to 8. In a case where the host cell is *Escherichia coli*, for example, LB culture medium or M9 culture medium (Mol. Clo., Cold Spring Harbor Laboratory, 2001, Vol. 3, A2.2) can be preferably used as the culture medium. The culturing is generally performed at approximately 14° C. to 39° C. for approximately 3 to 24 hours under optional ventilation or stirring. In a case where the host cell is yeast, for example, Burkholder minimal medium (Bostian K A et al., Proc Natl Acad Sci USA. 1980, Vol. 77, p. 4504-4508) can be used as the culture medium. The culturing is generally performed at approximately 20° C. to 35° C. for approximately 14 to 144 hours under optional ventilation or stirring. The multispecific antibody of the present invention can be expressed by the culturing as described above.

The method for producing the multispecific antibody of the present invention can further include, in addition to the steps of culturing the transfected host cell of the present invention to express the multispecific antibody, a step of recovering, for example, isolating or purifying a multispecific antibody from the transfected host cell and/or the culture supernatant. Examples of the isolation or purification method include methods using solubility such as salting-out and a solvent precipitation method, methods using the difference in molecular weight such as dialysis, ultrafiltration, and gel filtration, methods using an electric charge such as ion exchange chromatography and hydroxylapatite chromatography, methods using specific affinity such as affinity chromatography, methods using the difference in hydrophobicity such as reverse phase high performance liquid chromatography, and methods using the difference in the isoelectric point such as isoelectric focusing electrophoresis. For example, the antibody accumulated in the culture supernatant can be purified by various types of chromatography, for example, column chromatography using a Protein A column or a Protein G column.

The multispecific antibody of the present invention also include a multispecific antibody produced by the method of producing a multispecific antibody of the present invention.

Pharmaceutical Composition of Present Invention

The present invention also provides a pharmaceutical composition (also referred to as "the pharmaceutical composition of the present invention") including the multispecific antibody of the present invention and a pharmaceutically acceptable excipient. The pharmaceutical composition of the present invention can be prepared by a generally used method with an excipient generally used in the field, that is, a pharmaceutical excipient, a pharmaceutical carrier, or the like. Examples of a dosage form of the pharmaceutical composition include parenteral drug such as an injection drug and a drip infusion drug, and these can be administered by intravenous administration, subcutaneous administration, intramuscular administration, or the like. In the drug formulation, an excipient, a carrier, an additive, and the like can be used according to the dosage form within a pharmaceutically acceptable range.

The pharmaceutical composition of the present invention may include a multispecific antibody generated by a post-translational modification of the multispecific antibody of the present invention. The pharmaceutical composition of the present invention may include a plurality of kinds of multispecific antibodies of the present invention. In one embodiment, the pharmaceutical composition of the present invention contain the multispecific antibody of the present invention and a multispecific antibody generated by a post-translational modification of the multispecific antibody. In one embodiment, the multispecific antibody generated by the post-translational modification includes N-terminal pyroglutamylation of the polypeptide of (a) and/or deletion of C-terminal lysine of the heavy chain of an antibody binding to Fn14 (also simply referred to as an "Fn14 antibody").

In one embodiment, the pharmaceutical composition of the present invention contains the multispecific antibody of the present invention and/or a multispecific antibody generated by a post-translational modification of the multispecific antibody, and the multispecific antibody of the present invention includes:

(a) a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, and (b) an antibody binding to Fn14 or an antigen-binding fragment thereof includes a heavy chain variable region consisting of the amino acid sequence of amino acid numbers 273 to 390 of SEQ ID NO: 2 and a light chain variable region consisting of the amino acid sequence of amino acid numbers 1 to 108 of SEQ ID NO: 4.

In one embodiment, the post-translational modification is N-terminal pyroglutamylation of the polypeptide of (a) and/or deletion of C-terminal lysine of a heavy chain of the Fn14 antibody.

In one embodiment, the pharmaceutical composition of the present invention contains the multispecific antibody of the present invention and/or a multispecific antibody generated by a post-translational modification of the multispecific antibody, and the multispecific antibody of the present invention includes:

(a) a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, and (b) an antibody binding to Fn14 including a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E, and a light chain including a light chain variable region consisting of the amino acid sequence of amino acid numbers 1 to 108 of SEQ ID NO: 4 and a light chain constant region.

In one embodiment, the post-translational modification is N-terminal pyroglutamylation of the polypeptide of (a) and/or deletion of C-terminal lysine of a heavy chain of the Fn14 antibody.

In one embodiment, the pharmaceutical composition of the present invention contains the multispecific antibody of the present invention and/or a multispecific antibody generated by a post-translational modification of the multispecific antibody, and the multispecific antibody of the present invention includes:

(a) a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, and (b) an antibody binding to Fn14 including a heavy chain consisting of the amino acid sequence set forth in amino acid numbers 273 to 720 of SEQ ID NO: 2 and a light chain consisting of the amino acid sequence set forth in SEQ ID NO: 4.

In one embodiment, the post-translational modification is N-terminal pyroglutamylation of the polypeptide of (a) and/or deletion of C-terminal lysine of a heavy chain of the Fn14 antibody.

In one embodiment, the pharmaceutical composition of the present invention contains the multispecific antibody of the present invention and/or a multispecific antibody generated by a post-translational modification of the multispecific antibody, and the multispecific antibody of the present invention includes:

(a) a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, in which the C terminal of the first VHH is linked to the N terminal of the second VHH via a peptide linker, and (b) an antibody binding to Fn14 or an antigen-binding fragment thereof includes a heavy chain variable region consisting of the amino acid sequence of amino acid numbers 273 to 390 of SEQ ID NO: 2 and a light chain variable region consisting of the amino acid sequence of amino acid numbers 1 to 108 of SEQ ID NO: 4.

In one embodiment, the post-translational modification is N-terminal pyroglutamylation of the polypeptide of (a) and/or deletion of C-terminal lysine of a heavy chain of the Fn14 antibody.

In one embodiment, the pharmaceutical composition of the present invention contains the multispecific antibody of the present invention and/or a multispecific antibody generated by a post-translational modification of the multispecific antibody, and the multispecific antibody of the present invention includes:

(a) a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, in which the C terminal of the first VHH is linked to the N terminal of the second VHH via a peptide linker, and (b) an antibody binding to Fn14 including a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E, and a light chain including a light chain variable region consisting of the amino acid sequence of amino acid numbers 1 to 108 of SEQ ID NO: 4 and a light chain constant region.

In one embodiment, the post-translational modification is N-terminal pyroglutamylation of the polypeptide of (a) and/or deletion of C-terminal lysine of a heavy chain of the Fn14 antibody.

In one embodiment, the pharmaceutical composition of the present invention contains the multispecific antibody of the present invention and/or a multispecific antibody generated by a post-translational modification of the multispecific antibody, and the multispecific antibody of the present invention includes:

(a) a polypeptide including a first VHH consisting of the amino acid sequence of amino acid numbers 1 to 116 of SEQ ID NO: 2 and a second VHH consisting of the amino acid sequence of amino acid numbers 142 to 262 of SEQ ID NO: 2, in which the C terminal of the first VHH is linked to the N terminal of the second VHH via a peptide linker, and (b) an antibody binding to Fn14 including a heavy chain consisting of the amino acid sequence set forth in amino acid numbers 273 to 720 of SEQ ID NO: 2 and a light chain consisting of the amino acid sequence set forth in SEQ ID NO: 4.

In one embodiment, the post-translational modification is N-terminal pyroglutamylation of the polypeptide of (a) and/or deletion of C-terminal lysine of a heavy chain of the Fn14 antibody.

In one embodiment, the pharmaceutical composition of the present invention contains the multispecific antibody of the present invention and/or a multispecific antibody generated by a post-translational modification of the multispecific antibody, and the multispecific antibody of the present invention includes:

(a) a polypeptide consisting of the amino acid sequence of amino acid numbers 1 to 262 of SEQ ID NO: 2, and (b) an antibody binding to Fn14 including an antibody binding to Fn14 including a heavy chain variable region consisting of the amino acid sequence of amino acid numbers 273 to 390 of SEQ ID NO: 2 and a light chain variable region consisting of the amino acid sequence of amino acid numbers 1 to 108 of SEQ ID NO: 4, or an antigen-binding fragment thereof.

In one embodiment, the post-translational modification is N-terminal pyroglutamylation of the polypeptide of (a) and/or deletion of C-terminal lysine of a heavy chain of the Fn14 antibody.

In one embodiment, the pharmaceutical composition of the present invention contains the multispecific antibody of the present invention and/or a multispecific antibody generated by a post-translational modification of the multispecific antibody, and the multispecific antibody of the present invention includes:

(a) a polypeptide consisting of the amino acid sequence of amino acid numbers 1 to 262 of SEQ ID NO: 2, and (b) an antibody binding to Fn14 including a heavy chain including a heavy chain variable region consisting of the amino acid sequence of amino acid numbers 273 to 390 of SEQ ID NO: 2 and a heavy chain constant region having amino acid mutations of L234A, L235A, M252Y, S254T, and T256E, and a light chain including a light chain variable region consisting of the amino acid sequence of amino acid numbers 1 to 108 of SEQ ID NO: 4 and a light chain constant region.

In one embodiment, the post-translational modification is N-terminal pyroglutamylation of the polypeptide of (a) and/or deletion of C-terminal lysine of a heavy chain of the Fn14 antibody.

In one embodiment, the pharmaceutical composition of the present invention contains the multispecific antibody of the present invention and/or a multispecific antibody generated by a post-translational modification of the multispecific antibody, and the multispecific antibody of the present invention includes:

(a) a polypeptide consisting of the amino acid sequence of amino acid numbers 1 to 262 of SEQ ID NO: 2, and (b) an antibody binding to Fn14 including a heavy chain consisting of the amino acid sequence set forth in amino acid numbers 273 to 720 of SEQ ID NO: 2 and a light chain consisting of the amino acid sequence set forth in SEQ ID NO: 4.

In one embodiment, the post-translational modification is N-terminal pyroglutamylation of the polypeptide of (a) and/or deletion of C-terminal lysine of a heavy chain of the Fn14 antibody.

In one embodiment, the pharmaceutical composition of the present invention is a pharmaceutical composition containing the multispecific antibody of the present invention and/or a multispecific antibody generated by a post-translational modification of the multispecific antibody, in which the multispecific antibody of the present invention includes a polypeptide consisting of the amino acid sequence of SEQ ID NO: 2 and a light chain consisting of the amino acid sequence of SEQ ID NO: 4. In one embodiment, the post-translational modification is N-terminal pyroglutamylation of the polypeptide of (a) and/or deletion of C-terminal lysine of a heavy chain of the Fn14 antibody.

In one embodiment, the pharmaceutical composition of the present invention contains one kind or two or more kinds of multispecific antibodies selected from the following (c) to (f).

(c) A multispecific antibody including a polypeptide consisting of the amino acid sequence of amino acid numbers 1 to 719 of SEQ ID NO: 2 and a polypeptide consisting of the amino acid sequence set forth in SEQ ID NO: 4.

(d) A multispecific antibody including a polypeptide consisting of the amino acid sequence set forth in SEQ ID NO: 2, in which glutamic acid at the amino acid number 1 of SEQ ID NO: 2 is modified with pyroglutamic acid, and a polypeptide consisting of the amino acid sequence set forth in SEQ ID NO: 4.

(e) A multispecific antibody including a polypeptide consisting of the amino acid sequence of amino acid numbers 1 to 719 of SEQ ID NO: 2, in which glutamic acid at the amino acid number 1 of SEQ ID NO: 2 is modified with pyroglutamic acid, and a polypeptide consisting of the amino acid sequence set forth in SEQ ID NO: 4.

(f) A multispecific antibody including a polypeptide consisting of the amino acid sequence set forth in SEQ ID NO: 2 and a polypeptide consisting of the amino acid sequence set forth in SEQ ID NO: 4.

The amount of the multispecific antibody of the present invention added in the formulation varies depending on the degree of a patient's symptom, the age of a patient, a dosage form of a drug to be used, a binding titer of the antibody, or the like, and for example, the antibody or antigen-binding fragment thereof can be used such that the amount of the antibody or antigen-binding fragment thereof is approximately 0.001 mg/kg to 100 mg/kg during the administration.

The pharmaceutical composition of the present invention can be used as a prophylactic or therapeutic agent for diseases in which ActRIIA, ActRIIB, and Fn14 are involved in pathogenesis, such as inclusion body myositis.

The present invention includes a pharmaceutical composition for preventing or treating inclusion body myositis, the pharmaceutical composition including the multispecific antibody of the present invention. In addition, the present invention includes a method for preventing or treating inclusion body myositis, the method including administering a therapeutically effective amount of the multispecific antibody of the present invention. Moreover, the present invention also includes the multispecific antibody of the present invention for use in prevention or treatment of inclusion body myositis. Furthermore, the present invention includes a use of the multispecific antibody of the present invention in the production of a pharmaceutical composition for preventing or treating inclusion body myositis.

<Polypeptide Binding to ActRIIA and ActRIIB>

The present invention also provides the following polypeptide binding to ActRIIA and ActRIIB (hereinafter also referred to as "the ActRIIA/B-binding peptide of the present invention"):

a polypeptide binding to ActRIIA and ActRIIB, in which the polypeptide include a first VHH and a second VHH, binding to ActRIIA and ActRIIB, the first VHH includes CDR1 consisting of the amino acid sequence of amino acid numbers 31 to 35 of SEQ ID NO: 2, CDR2 consisting of the amino acid sequence of amino acid numbers 50 to 65 of SEQ ID NO: 2, and CDR3 consisting of the amino acid sequence of amino acid numbers 98 to 105 of SEQ ID NO: 2, and the second VHH includes CDR1 consisting of the amino acid sequence of amino acid numbers 172 to 176 of SEQ ID NO: 2, CDR2 consisting of the amino acid sequence of amino acid numbers 195 to 210 of SEQ ID NO: 2, and CDR3 consisting of the amino acid sequence of amino acid numbers 243 to 251 of SEQ ID NO: 2.

In one embodiment, the first VHH and the second VHH are humanized VHHs. In one embodiment, the first VHH consists of the amino acid sequence of amino acid numbers 1 to 116 of SEQ ID NO: 2 and the second VHH consists of the amino acid sequence of amino acid numbers 142 to 262 of SEQ ID NO: 2.

In the ActRIIA/B-binding peptide of the present invention, the C terminal of the first VHH may be linked to the N terminal of the second VHH, and the C terminal of the second VHH may be linked to the N terminal of the first VHH. In one embodiment, the C terminal of the first VHH is linked to the N terminal of the second VHH.

In the ActRIIA/B-binding peptide of the present invention, the first VHH and the second VHH may be directly linked or linked via a peptide linker. In one embodiment, the first VHH and the second VHH are linked via a peptide linker.

In one embodiment, the C terminal of the first VHH is linked to the N terminal of the second VHH via a peptide linker. In one embodiment, the first VHH and the second VHH are humanized VHHs, and the C terminal of the first VHH is linked to the N terminal of the second VHH via a peptide linker.

In one embodiment, the first VHH consists of the amino acid sequence of amino acid numbers 1 to 116 of SEQ ID NO: 2, the second VHH consists of the amino acid sequence of amino acid numbers 142 to 262 of SEQ ID NO: 2, and the C terminal of the first VHH is linked to the N terminal of the second VHH via a peptide linker.

The peptide linker that links the first VHH and the second VHH is not particularly limited, and for example, the peptide linker exemplified as the peptide linker that links the first VHH and the second VHH in the section <Multispecific Antibody of Present Invention> can be used. In one embodiment, the peptide linker that links the first VHH and the second VHH is (Gly·Gly·Gly·Gly·Ser (SEQ ID NO: 7))$_n$ [n is an integer of 1 to 5], and in one embodiment, the peptide linker that links the first VHH and the second VHH is (Gly·Gly·Gly·Gly·Ser)$_5$ (amino acid numbers 117 to 141 of SEQ ID NO: 2).

In one embodiment, the first VHH and the second VHH are humanized VHHs, the C terminal of the first VHH is linked to the N terminal of the second VHH via a peptide linker, and the peptide linker that links the first VHH and the second VHH is (Gly·Gly·Gly·Gly·Ser)$_5$ (amino acid numbers 117 to 141 of SEQ ID NO: 2). In one embodiment, the ActRIIA/B-binding peptide of the present invention consists of the amino acid sequence of amino acid numbers 1 to 262 of SEQ ID NO: 2

Any of those skilled in the art can manufacture a fused product from in which the ActRIIA/B-binding peptide of the present invention is fused with another peptide or protein, or can also prepare a modified product to which a modifier is bound, based on the present invention, and these fused products and modified products thereof are also included in the ActRIIA/B-binding peptide of the present invention. Other peptides or proteins used for the fusion are not particularly limited as long as the fused product binds to ActRIIA and ActRIIB, and examples thereof include an antibody or antigen-binding fragment thereof, human serum albumin, various tag peptides, artificial helix motif peptide, maltose-binding proteins, glutathione S transferase, various toxins, and other peptides or proteins capable of promoting multimerization. The modifier used for the modification is not particularly limited as long as the modified product binds to ActRIIA and ActRIIB and examples thereof include polyethylene glycol, sugar chains, phospholipids, liposomes, and low-molecular compounds. In one embodiment, the modifier used to modify the ActRIIA/B-binding peptide of the present invention is polyethylene glycol.

The ActRIIA/B-binding peptide of the present invention, and a fused product and a modified product thereof can be readily manufactured by those skilled in the art, using a method known in the art, based on sequence information of VHHs, other peptides or proteins (for example, an antibody) used in the fused product, and information on a modifier used in the modified product. The ActRIIA/B-binding peptide of the present invention is not particularly limited, but can be produced, for example, according to the method described in the section of <Method for Producing Multispecific Antibody of Present Invention>.

Specific examples are provided herein for reference in order to obtain further understanding of the present invention; however, these examples are for the purpose of illustration and the present invention is not limited thereto.

EXAMPLES

With regard to parts using commercially available kits, reagents, or the like, experiments were conducted according to an attached protocol unless otherwise specified.

Example 1: Acquisition of Single VHH

The present inventors immunized an alpaca multiple times with proteins including the extracellular domain of ActRIIB in order to acquire a VHH targeting the extracellular domain of ActRIIB. After completion of the immunization, blood was collected from the alpaca, alpaca peripheral blood lymphocytes were separated from the collected blood sample, and an immune library for a phage display was constructed according to a known method (Miyazaki N et al., J Biochem. 2015, Vol. 158, p. 205-215). Biopanning for the extracellular domain of ActRIIB using the phage display was performed on a protein including the extracellular domain of ActRIIB, a stably expressing cell line in which a human ActRIIB gene (NCBI accession number: NM_001106.4) was introduced into CHO cells (hereinafter referred to as ActRIIB/CHO cells), and a stably expressing cell line in which a human ActRIIB gene (NCBI accession number: NM_001106.4) was introduced into HEK293 cells (hereinafter referred to as ActRIIB/HEK293 cells). Biopanning targeting a protein including the extracellular domain of ActRIIB was performed according to a known method (Miyazaki N et al., J Biochem. 2015, Vol. 158, p. 205-215). In the biopanning targeting the ActRIIB/CHO cells or the ActRIIB/HEK293 cells, a phage bound to each cell was acquired by a method in which the phage library and each cell were mixed and repeatedly subjected to a washing operation several times, and then the phage bound to the cell was eluted from the phage/cell complex with an acid. A plurality of phages binding to the extracellular domain of ActRIIB were acquired by the biopanning. The VHH-encoding genes were cloned from the acquired phage and sequenced.

Example 2: Acquisition of Tandem VHHs

Among the VHHs obtained in Example 1, a plurality of libraries in which genes encoding any two VHHs were linked to genes encoding peptide linkers with various lengths (also referred to as GS linkers) composed of Gly and Ser for the phage display were constructed and subjected to biopanning in the same manner as in Example 1. Biopanning for the extracellular domain of ActRIIA and the extracellular domain of ActRIIB using the phage display was performed on a protein including the extracellular domain of ActRIIA, a protein including the extracellular domain of ActRIIB, a stably expressing cell line in which a human ActRIIA gene (NCBI accession number: AB529011.1) was introduced into CHO cells (hereinafter referred to as ActRIIA/CHO cells), and ActRIIB/CHO cells. As a result of evaluating a plurality of tandem VHHs, a tandem VHH binding to the extracellular domains of ActRIIA and ActRIIB was acquired. The tandem VHH is referred to as 75E9. Then, the tandem VHH 75E9 was humanized according to examples of International Publication No. 2006/122825 and the like. This is referred to as a humanized tandem VHH 75E9.

The amino acid sequence of the humanized tandem VHH 75E9 is set forth in amino acid numbers 1 to 262 of SEQ ID NO: 2. The first VHH in the humanized tandem VHH 75E9 set forth in amino acid numbers 1 to 262 of SEQ ID NO: 2 consists of the amino acid sequence of amino acid numbers 1 to 116 of SEQ ID NO: 2 and the second VHH consists of the amino acid sequence of amino acid numbers 142 to 262 of SEQ ID NO: 2.

CDR1, CDR2, and CDR3 of the first VHH of the humanized tandem VHH 75E9 consist of amino acid sequences from amino acid numbers 31 to 35, 50 to 65, and 98 to 105 of SEQ ID NO: 2, respectively. CDR1, CDR2, and CDR3 of the second VHH of the humanized tandem VHH 75E9 consist of amino acid sequences from amino acid numbers 172 to 176, 195 to 210, and 243 to 251 of SEQ ID NO: 2, respectively.

Example 3: Acquisition of Anti-Fn14 Antibody

In order to acquire an antibody binding to human Fn14 expressed on a cell surface, the present inventors prepared a human Fc fusion protein including the extracellular domain of human Fn14 according to Example 1 of International Publication No. 2020/090892, constructed a stably expressing cell line in which a human Fn14 gene (NCBI accession number: NM_016639) was introduced into Jurkat cells (hereinafter referred to as Fn14/Jurkat cells), and used for immunization and screening. Furthermore, an antibody was developed using a human monoclonal antibody developing technology "VelocImmune" (VelocImmune antibody technology: Regeneron Pharmaceuticals, Inc. (U.S. Pat. No. 6,596,541)) mouse. The antibody obtained by the VelocImmune technology is an antibody having a variable region of a human antibody and a constant region of a mouse antibody. VelocImmune mice were immunized with an adjuvant for causing an immune reaction together with a human Fn14 protein in which a human Fc region was cut and removed from the human Fc fusion protein including the extracellular domain of a human Fn14 prepared above by using FabRICATOR (Sigma, 77661), and the Fn14/Jurkat cells, alternately. Lymphocytes collected from the lymph node of the immunized mouse were fused with mouse-derived myeloma cells SP2/0-Ag14 (ATCC: CRL-1581) according to a standard method to generate hybridomas, and the hybridomas were monocloned. Hybridomas producing an antibody, which binds to human Fn14 and Fn14/Jurkat cells and suppresses the NF-κB activation induced by TWEAK stimulation (hereinafter referred to as TWEAK-induced NF-κB activation in Examples below), were selected. Further, the genes encoding the heavy chain and the light chain of the antibody were cloned from the hybridomas, and the sequence was determined. A gene encoding a human Igγ1 constant region having amino acid mutations of L234A and L235A, and a gene encoding a signal sequence (Whittle N et al., Protein Eng. 1987, Vol. 1, p. 499-505) were linked to the 3' side and the 5' side of the gene encoding the heavy chain variable region of this antibody (corresponding to a nucleotide sequence encoding amino acid numbers 273 to 390 of SEQ ID NO: 2) (SEQ ID NO: 13), respectively, and inserted into a GS vector pEE6.4 (Lonza). SEQ ID NO: 14 is a sequence obtained by translating SEQ ID NO: 13 into amino acids. In addition, a gene encoding the signal sequence and a gene encoding the constant region of a human κ chain (corresponding to a nucleotide sequence encoding amino acid numbers 109 to 214 of SEQ ID NO: 4) were linked to the 5' side and the 3' side of the gene encoding the light chain variable region of this antibody (corresponding to a nucleotide sequence encoding amino acid numbers 1 to 108 of SEQ ID NO: 4), respectively, and inserted into GS vector pEE12.4 (Lonza). A double-gene vector (hereinafter referred to as DGV) into which both the heavy chain and light chain genes were inserted was constructed from these GS vectors. The antibody was purified from the culture supernatant of CHO-K1SV cells transfected with this vector according to a standard method. This antibody is referred to as STF8-1.

The heavy chain variable region of STF8-1 consists of the amino acid sequence of amino acid numbers 273 to 390 of SEQ ID NO: 2. The light chain variable region of STF8-1 consists of the amino acid sequence of amino acid numbers 1 to 108 of SEQ ID NO: 4.

CDR1, CDR2, and CDR3 of the heavy chain variable region of STF8-1 consist of amino acid sequences from amino acid numbers 303 to 307, 322 to 338, and 371 to 379 of SEQ ID NO: 2, respectively. CDR1, CDR2, and CDR3 of the light chain variable region of STF8-1 consist of amino acid sequences from amino acid numbers 24 to 34, 50 to 56, and 89 to 97 of SEQ ID NO: 4, respectively.

Example 4: Production of Humanized 75E9STF8-1

A polynucleotide in which a gene encoding the signal sequence, a gene encoding humanized tandem VHH 75E9 (corresponding to nucleotide numbers 1 to 786 of SEQ ID NO: 1), a gene encoding a GS linker (corresponding to nucleotide numbers 787 to 816 of SEQ ID NO: 1), a gene encoding the heavy chain variable region of STF8-1 (corresponding to nucleotide numbers 817 to 1170 of SEQ ID NO: 1), and a gene (corresponding to nucleotide numbers 1171 to 2160 in SEQ ID NO: 1) encoding a human Igγ1 constant region having amino acid mutations of L234A and L235A and amino acid mutations of M252Y, S254T, and T256E (International Publication No. 2002/060919) were linked in this order was inserted into a GS vector pEE6.4 (Lonza). In addition, a gene encoding the signal sequence and a gene (corresponding to nucleotide numbers 325 to 642 of SEQ ID NO: 3) encoding a constant region of a human κ chain were each linked to the 5' side and the 3' side of a gene (corresponding to nucleotide numbers 1 to 324 of SEQ ID NO: 3) of a light chain variable region of STF8-1, and inserted into a GS vector pEE12.4 (Lonza). DGVs into which both the heavy and light chain genes were inserted were constructed from these GS vectors. The antibody was purified from the culture supernatant of CHO-K1SV cells transfected with this vector according to a standard method. This antibody is referred to as humanized 75E9STF8-1.

Example 5: Evaluation of Binding Activity of Humanized 75E9STF8-1

The binding activities of the humanized 75E9STF8-1 obtained in Example 4 to ActRIIA, ActRIIB, and Fn14 were evaluated. ActRIIA-His (LifeSpan Biosciences, LS-G39063), ActRIIB-His (LifeSpan Biosciences, LS-G38834), and the human Fc fusion proteins including the extracellular domain of human Fn14 prepared in Example 3 were each diluted to 1 μg/mL with phosphate-buffered physiological saline (PBS), each added to a Maxisorp 384-well transparent plate (Nunc, 464718) at 15 μL/well, and incubated at 4° C. overnight for immobilization. On the next day, the solid phase liquid was removed and washing was performed with a 0.05% Tween-20-containing Tris-buffered physiological saline (TBS-T). Thereafter, PBS including 20% Blocking One (Nacalai tesque, Inc., 03953-95) was added thereto at 50 μL/well, and the mixture was left to stand at room temperature for 1 hour and then washed with TBS-T. Dilution series of humanized 75E9STF8-1 were prepared by dilution in 12 steps at a 4-fold common ratio from the maximum concentration of 30

μg/mL, and added at 20 μL/well. TBS-T including 5% Blocking One was used as a diluent. After incubation for 1 hour at room temperature, washing was performed with TBS-T. As a detection antibody, Goat Anti-Human Kappa, Mouse ads-HRP (SouthernBiotech, 2061-05) which had been 4,000-fold diluted with a diluent (TBS-T including 5% Blocking One) was added at 20 μL/well. After incubating at room temperature for 1.5 hours, the cells were washed with TBS-T, TMB+Substrate-Chromogen (DAKO, S159985) was added thereto, the mixture was left to stand, 1 M sulfuric acid was added thereto to stop the reaction, and the absorbance at 450 nm was measured with Infinite (registered trademark) 200 Pro (TECAN).

As a result, humanized 75E9STF8-1 bound to ActRIIA-His (EC50=5.03 ng/mL), ActRIIB-His (EC50=9.24 ng/mL), and a human Fc fusion protein including the extracellular domain of human Fn14 (EC50=23.3 ng/mL).

Example 6: Evaluation of Smad Phosphorylation Inhibition of Humanized 75E9STF8-1

The inhibitory action of humanized 75E9STF8-1 on myostatin-induced Smad3 phosphorylation in ActRIIA and ActRIIB was evaluated. A stably expressing cell line in which a human ActRIIA gene (NCBI accession number: AB529011.1) was introduced into HEK293 cells (hereinafter referred to as ActRIIA/H1EK293 cells), and ActRIIB/HEK293 cells were used for evaluation.

ActRIIA/HEK293 cells or ActRIIB/HEK293 cells were suspended in a 10% fetal bovine serum-containing DMEM (Sigma, D6429) at $2\times10^5$ cells/mL, and seeded on a collagen I-coated 96-well plate (IWAKI, 4860-010) at 100 μL/well. The resultant was cultured overnight in a $CO_2$ incubator set at 37° C. and 5% $CO_2$. After the culturing, the medium was removed by centrifugation, and 80 μL of a 2% fetal bovine serum-containing DMEM was added to each well. The resultant was cultured overnight in a $CO_2$ incubator under the same conditions as above. Dilution series of the humanized 75E9STF8-1 were prepared by dilution in 8 steps at an about 3-fold common ratio from the maximum concentration of 300 nmol/L for the ActRIIA/HEK293 cells and from the maximum concentration of 1,000 nmol/L for the ActRIIB/HEK293 cells, and added at 10 μL/well. In addition, the same dilution series of Bimagrumab were added as a control. A 2% fetal bovine serum-containing DMEM was used as a dilution solvent. The resultant was cultured for 15 minutes in a $CO_2$ incubator under the same conditions as above. Thereafter, 10 μL/well of myostatin (PEPROTECH, 120-00) prepared in a 2% fetal bovine serum-containing DMEM was added to a final concentration of 100 ng/mL. After culturing for 1 hour in a $CO_2$ incubator under the same conditions as above, the medium was removed by centrifugation, a lysis buffer in an AlphaLISA (registered trademark) SureFire (registered trademark) Ultra™ SMAD3 (p-Ser423/425) assay kit (PerkinElmer, ALSU-PSM3) was added to the resultant at 50 μL/well and dissolved by stirring at room temperature for 10 minutes to lyse the cells. Phosphorylated Smad3 in the cell lysate was detected using the kit. The results are expressed in terms of an inhibition rate in a case where a value measured under the condition of 100 ng/mL myostatin stimulation and a value measured in the absence of myostatin are set to 0% inhibition and 100% inhibition, respectively. Measurements in the absence of myostatin were carried out by adding a medium instead of myostatin. Furthermore, the data represent an average value of 2 trials (each trial was carried out in duplicate).

Figure 1B:
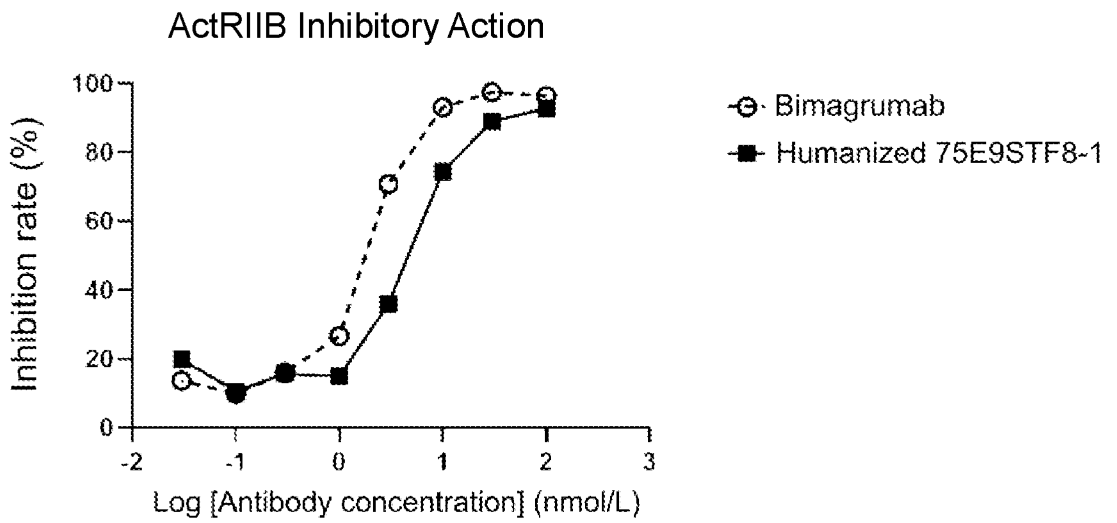
FIG. 1B shows an inhibitory action on myostatin-induced Smad3 phosphorylation in ActRIIB/HEK293 cells (ActRIIB inhibitory action). The ordinate indicates the inhibition rate of Smad3 phosphorylation by 100 ng/mL of myostatin (a value measured under stimulation conditions of 100 ng/mL myostatin is set to 0% inhibition and a value measured in the absence of myostatin is set to 100% inhibition). The abscissa indicates a logarithm of the concentration (nmol/L) of the antibody. Furthermore, the data represent an average value of 2 trials (each trial was carried out in duplicate).

As a result, the humanized 75E9STF8-1 inhibited myostatin-induced Smad3 phosphorylation in the ActRIIA/HEK293 cells and ActRIIB/HEK293 cells (FIGS. 1A and 1).

Example 7: Evaluation of Antagonistic and Agonistic Activities of Humanized 75E9STF8-1

Activation of Fn14 in the presence or absence of TWEAK activates NF-κB as a downstream signal. In order to evaluate the antagonistic activity of humanized 75E9STF8-1, this signal was used as an index to evaluate the inhibitory action of TWEAK-induced NF-κB activation in human Fn14. In addition, as an evaluation of the agonistic activity of humanized 75E9STF8-1, the NF-κB activation action was evaluated in the absence of TWEAK. Specifically, the action of humanized 75E9STF8-1 on NF-κB activation in the presence or absence of TWEAK was evaluated in a reporter assay. HEK293 cells into which a luciferase reporter vector pGL4.32 (Promega K. K., E8491) having an NF-κB transcription responsive sequence incorporated thereinto had been stably introduced (hereinafter referred to as NF-κB/HEK293 cells) were generated and used for evaluation.

The NF-κB/HEK293 cells were suspended in a 10% fetal bovine serum-containing DMEM (Sigma, D6429) at $1.25\times10^5$ cells/mL and seeded at 80 μL/well in a clear bottom white 96-well plate (Corning Incorporated, 3610). The resultant was cultured for 2 hours in a $CO_2$ incubator set at 37° C. and 5% $CO_2$. Dilution series of the humanized 75E9STF8-1 in the medium were prepared and then added at 10 μL/well. The final concentration in each well was set in 11 steps (at an about 3-fold common ratio) from the maximum concentration of 100 nmol/L for the antagonistic activity evaluation, and 11 steps (at an about 3-fold common ratio) from the maximum concentration of 300 nmol/L for the agonistic activity evaluation. In addition, the same dilution series of STF8-1 were added as a control. In the antagonistic activity evaluation, 10 μL of TWEAK (PEPROTECH, 310-06) prepared in the medium was added to each well to a final concentration of 100 ng/mL. For the agonistic activity evaluation, 10 μL of the medium was added to each well. After culturing overnight at 37° C. with 5% $CO_2$, a luciferase expression level was measured using a luciferase measurement reagent ONE-Glo™ Luciferase Assay System (Promega K.K., E6120) to quantify the NF-κB activation. The results are expressed in terms of an inhibition rate in a case where a value measured under the condition of 100 ng/mL of TWEAK stimulation is set to 0% inhibition and a value measured in the absence of TWEAK is set to 100% inhibition for in the antagonistic activity evaluation, and expressed in terms of an activation rate in a case where a value measured under the condition of 100 ng/mL of TWEAK stimulation is set to 100% and a value measured in the absence of TWEAK is set to 0% for in the agonistic activity evaluation. Measurements in the absence of TWEAK were performed by adding a medium instead of TWEAK. Furthermore, the data represent an average value of 2 trials (each trial was carried out in duplicate).

Figure 2A:
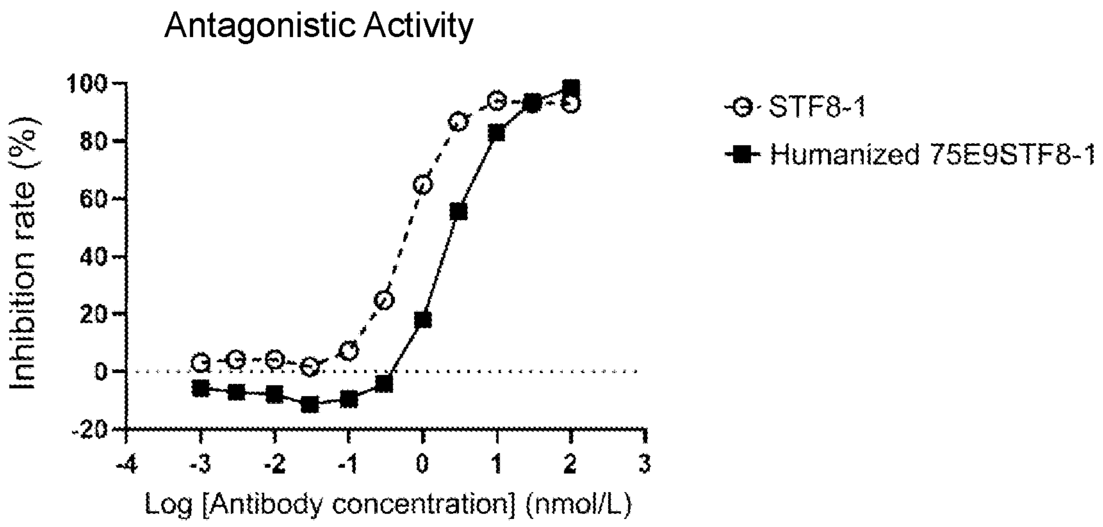
FIG. 2A shows an antagonistic activity against TWEAK-induced NF-κB activation in NF-κB/HEK293 cells and FIG. 2B shows an agonistic activity on Fn14 in NF-κB/HEK293 cells. The ordinate indicates an inhibition rate (a value measured under 100 ng/mL of TWEAK stimulation conditions is set to 0% inhibition, and a value measured in the absence of TWEAK is set to 100% inhibition) against NF-κB activation by 100 ng/mL of TWEAK in FIG. 2A, and a relative activation rate by an evaluation antibody in the absence of TWEAK in a case where a value measured under stimulation conditions of 100 ng/mL of TWEAK is set to 100% and a value measured in the absence of TWEAK is set to 0% in FIG. 2B. The abscissa indicates a logarithm of the concentration (nmol/L) of the antibody. Furthermore, the data represent an average value of 2 trials (each trial was carried out in duplicate).
Figure 2B:
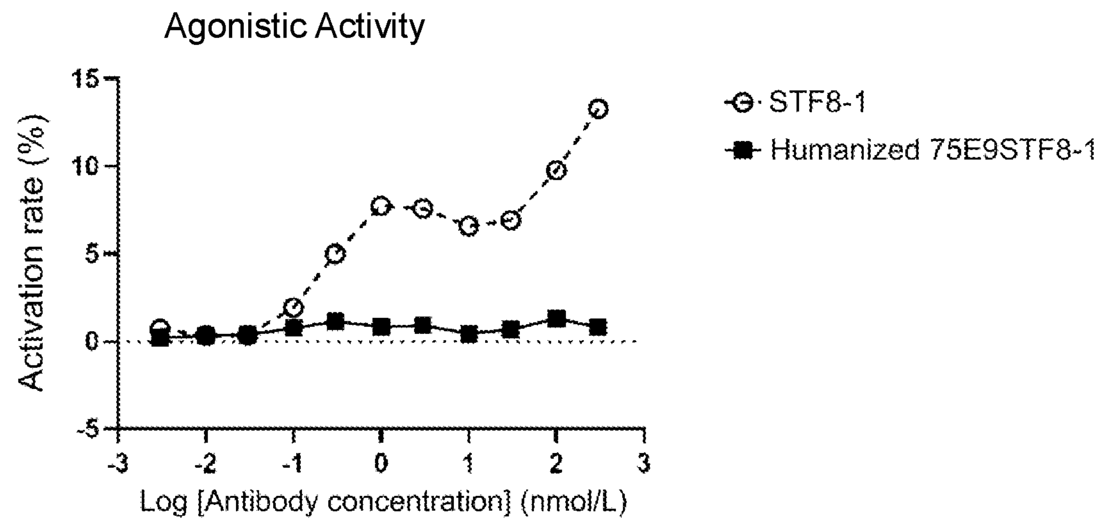

As a result, the humanized 75E9STF8-1 completely inhibited Fn14-mediated NF-κB activation by 100 ng/mL of TWEAK. In addition, the humanized 75E9STF8-1 did not induce NF-κB activation in the absence of TWEAK (FIGS. 2A and 2B). Thus, it was confirmed that the humanized 75E9STF8-1 has the antagonistic activity, but not the agonistic activity.

Example 8: Preparation and Functional Evaluation of Antibody Used in Mouse in Vivo Pharmacological Efficacy Evaluation For the mouse in vivo pharmacological efficacy evaluation, 75E9 (mFc), STF8-1 (mFc), and 75E9STF8-1 (mFc) were prepared, respectively, based on the amino acid sequences of humanized tandem VHH 75E9, STF8-1, and humanized 75E9STF8-1. 75E9 (mFc) is an antibody in which Hinge, CH2, and CH3 of a mouse IgG1 heavy chain constant region are linked to the C terminal of 75E9 of the tandem VHH in Example 2 (SEQ ID NO: 15). STF8-1 (mFc) is an antibody in which the constant region of STF8-1 of Example 3 is substituted with mouse constant regions for both heavy and light chains (the heavy chain of STF8-1 (mFc) is set forth in SEQ ID NO: 16 and the light chain of STF8-1 (mFc) is set forth in SEQ ID NO: 17). 75E9STF8-1 (mFc) is an antibody consisting of a polypeptide (SEQ ID NO: 18) in which the N terminal of the STF8-1 (mFc) heavy chain is linked to the C terminal of 75E9 in Example 2 with a peptide linker (Gly·Gly·Gly·Gly·Ser (SEQ ID NO: 7))$_2$ and a light chain of STF8-1 (mFc).

The amino acid sequences of CDR1, CDR2, and CDR3 of the first VHH of 75E9STF8-1 (mFc) and CDR1, CDR2, and CDR3 of the second VHH of 75E9STF8-1 (mFc) are the same as those of CDR1, CDR2, and CDR3 of the first VHH of humanized 75E9STF8-1 and CDR1, CDR2, and CDR3 of the second VHH of humanized 75E9STF8-1, respectively. Furthermore, the heavy chain variable region and the light chain variable region of STF8-1 (mFc) included in 75E9STF8-1 (mFc) are the same as those of the heavy chain variable region and the light chain variable region of STF8-1 included in humanized 75E9STF8-1, respectively.

It was confirmed that 75E9 (mFc) and 75E9STF8-1 (mFc) were subjected to the functional evaluation described in Example 6 and confirmed to have an Smad phosphorylation inhibitory activity. In addition, the functional evaluation described in Example 7 was performed, and it was confirmed that STF8-1 (mFc) and 75E9STF8-1 (mFc) had an antagonistic activity and 75E9STF8-1 (mFc) had no agonistic activity.

Example 9: In Vivo Pharmacological Efficacy Evaluation for Steroid-Induced Myopathy Model Mice In mice, the in vivo pharmacological efficacy on muscle atrophy and muscle function were evaluated using a muscle weight and a grip strength as indices. A steroid-induced myopathy model (SIM model) by continuous administration of steroid was used as a muscle atrophy model animal, and the limb grip strength and the weight of an isolated quadriceps femoris muscle were measured after 14 days from repeated administration of the test substance.

The body weight and the grip strength of mice were measured, and 10 mice were assigned to each group so that the body weights and the grip strengths were equal among the groups. The groups are configured with a total of six groups of one normal group and five SIM model groups, in which the five SIM model groups are a vehicle-administered group, a 75E9 (mFc) group, an STF8-1 (mFc) group, a 75E9 (mFc)+STF8-1 (mFc) group, and a 75E9STF8-1 (mFc) group. Corticosterone (dissolved in filtered water mixed with 1% ethanol at a concentration of 100 μg/mL) was administered continuously to the SIM model group by free drinking for 14 days to induce muscle atrophy. The normal group was allowed to freely drink filtered water. Administrations of a test substance 1 and test substance 2 were started on the same day as the administration of corticosterone. The details of administration of the test substance for each group are shown in Table 1. The dose of the 75E9STF8-1 (mFc) group was set so that the molar concentration was approximately the same as the dose of each group administered alone. On the 14$^{th}$ day after the start of administration of the test substance, the grip strength was measured using a small animal grip strength measuring device (MELQUEST Ltd., GPM-100). Thereafter, the mouse was exsanguinated to death under anesthesia, and the quadriceps femoris muscle was removed and weighed.

TABLE 1

| | Group | Test substance 1 (once a week, intraperitoneal administration, 20 mL/kg) | Test substance 2 (three times a week, subcutaneous administration, 10 mL/kg) |
|---|---|---|---|
| | Normal group | Vehicle (PBS) | Vehicle (PBS) |
| SIM model | Vehicle-administered group | Vehicle (PBS) | Vehicle (PBS) |
| | 75E9 (mFc) group | 75E9 (mFc) 100 mg/kg | Vehicle (PBS) |
| | STF8-1 (mFc) group | Vehicle (PBS) | STF8-1 (mFc) 100 mg/kg |
| | 75E9 (mFc) + STF8-1 (mFc) group | 75E9 (mFc) 100 mg/kg | STF8-1 (mFc) 100 mg/kg |
| | 75E9STF8-1 (mFc) group | 75E9STF8-1 (mFc) 140 mg/kg | Vehicle (PBS) |

Figure 3A:
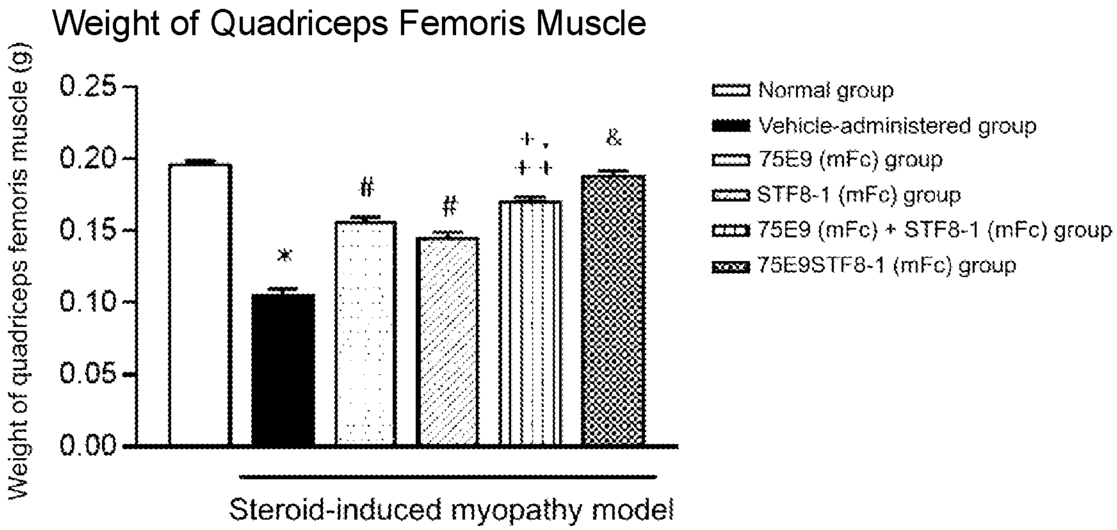
FIG. 3A shows weights of quadriceps femoris muscles after 14 days from the start of administration of a steroid and a test substance in steroid-induced myopathy model mice and FIG. 3B shows grip strengths after 14 days from the start of administration of a steroid and a test substance in steroid-induced myopathy model mice. The ordinate indicates a measured weight (g) of an isolated quadriceps femoris muscle in FIG. 3A and a limb grip strength (kg) in FIG. 3B. The data represent a mean±SEM of 10 cases in each group. *P<0.05 versus normal group, #P<0.05 versus vehicle-administered group, +P<0.05 versus 75E9 (mFc) group, ++P<0.05 versus STF8-1 (mFc) group, and P<0.05 versus 75E9 (mFc)+STF8-1 (mFc) group, all by a Student's t-test.
Figure 3B:
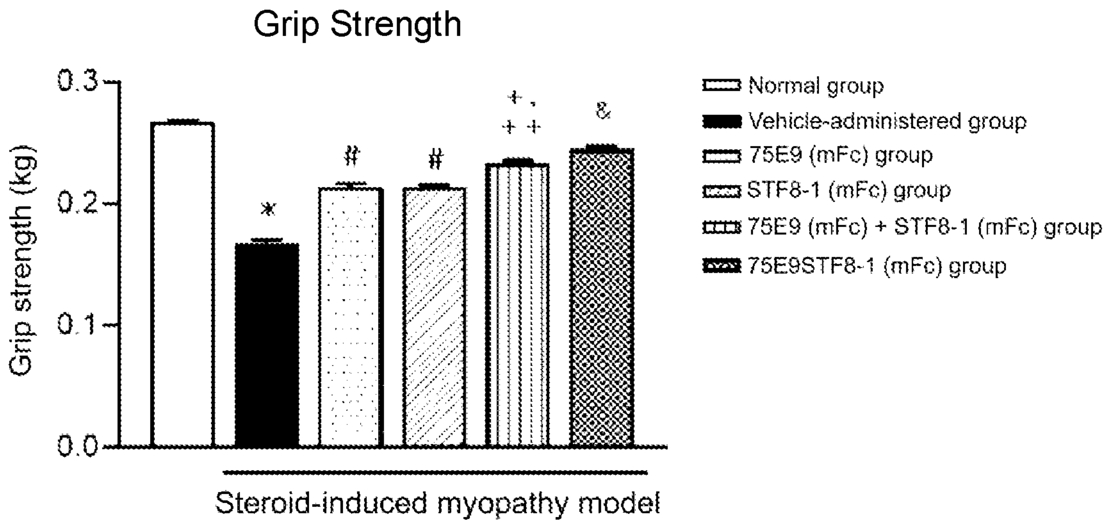

As a result, 75E9 (mFc) or STF8-1 (mFc) partially suppressed the skeletal muscle atrophy and decrease of the grip strength in the SIM model. Furthermore, a mixed treatment of 75E9 (mFc) and STF8-1 (mFc) exhibited significantly stronger inhibitory actions on the skeletal muscle atrophy and the grip strength reduction than the administration of each alone. In addition, 75E9STF8-1 (mFc) exhibited significantly stronger inhibitory actions on the skeletal muscle atrophy and the grip strength reduction than the mixed treatment of 75E9 (mFc) and STF8-1 (mFc) (FIGS. 3A and 3B).

Example 10: In Vivo Pharmacological Efficacy Evaluation for Steroid-Induced Myopathy Model Monkeys In vivo pharmacological efficacy on a lean thigh weight was evaluated in a cynomolgus monkey in a steroid-induced myopathy model after 4 weeks from administration of the test substance. It is noted that the lean weight is a total weight of muscle, bone, and blood, excluding fat, and is known to correlate with the skeletal muscle weight (Walowski C O et al., Nutrients. 2020, Vol. 12, 755).

The lean thigh weight of the cynomolgus monkey was measured using a bone densitometer (Discovery C, Hologic, Inc.) using dual energy X-ray absorptiometry, and the monkeys were equally divided into four groups. The groups are configured with a total of four groups of a normal group (n=2) and three SIM model groups (n=3 for each group), and the three groups of the SIM models are a vehicle-administered group, a humanized 75E9STF8-1 group, and a Bimagrumab group. Prednisolone (30 mg/3 mL/kg) was subcutaneously administered to the back of the SIM model group twice a day for 4 to 5 days/week to induce muscle atrophy. Physiological saline was similarly subcutaneously administered to the back of the normal group. The test substance was PBS for the normal group and the vehicle-administered group, 40 mg/2.4 mL/kg of humanized 75E9STF8-1 for the humanized 75E9STF8-1 group, and 30 mg/2.4 mL/kg of Bimagrumab for the Bimagrumab group, each of which was intravenously administered on day 1 of the administration of prednisolone. The dosage was set so that the humanized 75E9STF8-1 and Bimagrumab were administered at the same number of moles. Measurement of the lean thigh weight was carried out after 4 weeks from the administration of the test substance. The lean weight of each of the left and right thighs was measured, and an average value thereof was used as the measured value of the individual.

Figure 4:
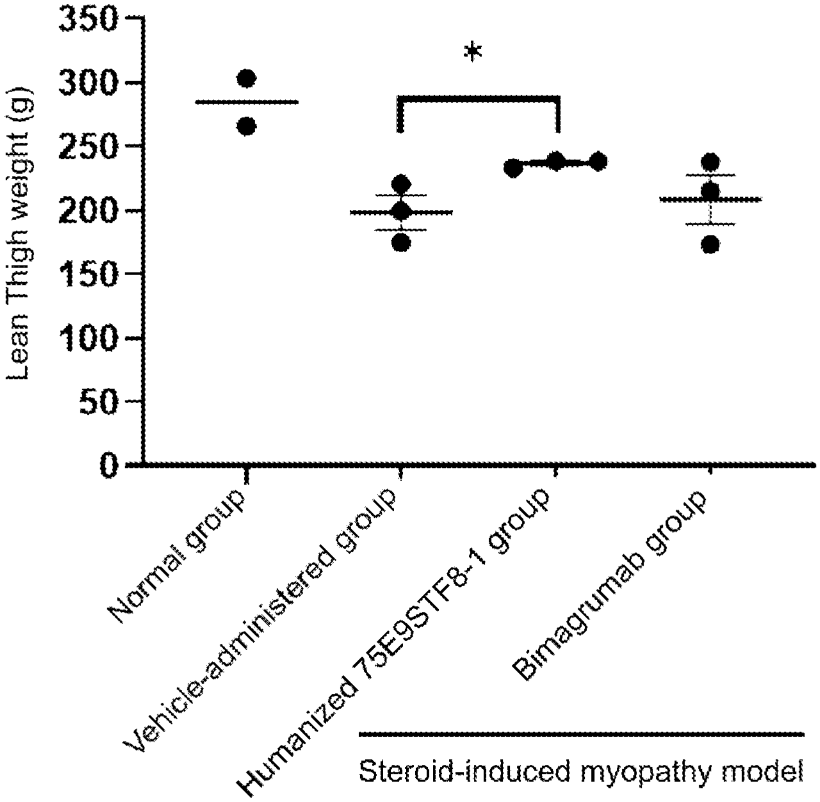
FIG. 4 shows the lean thigh weights after 4 weeks from the start of administration of a steroid and a test substance in steroid-induced myopathy model monkeys. The ordinate indicates the lean thigh weights (g) measured with a bone densitometer, using dual energy X-ray absorptiometry. Furthermore, the data for the normal group represent measured values and average values of 2 cases, and the data for each group of steroid-induced myopathy models represent measured values and average values±SEM of 3 cases in each group. *P<0.05 versus vehicle-administered group, Student's t-test.

As a result, in the SIM model monkeys, the lean thigh weight of the humanized 75E9STF8-1 group was significantly heavier than that of the vehicle-administered group. No significant difference was observed between the Bimagrumab group and the vehicle-administered group (FIG. 4).

INDUSTRIAL APPLICABILITY

The multispecific antibody of the present invention is useful for prevention or treatment of various diseases in which human ActRIIA, human ActRIIB, and human Fn14 are involved in pathogenesis. In addition, the polynucleotides, the expression vectors, the transfected host cells, and the method for producing the antibody of the present invention are expected to be useful for production of the multispecific antibody.

Sequence Listing Free Text

In the number heading <223> of the following sequence listing, description of "Artificial Sequence" is made. Specifically, the nucleotide sequence represented by SEQ ID NO: 1 in the sequence listing is a nucleotide sequence encoding a polypeptide including the first VHH of the multispecific antibody, the second VHH of the multispecific antibody, and the heavy chain of an antibody binding to Fn14 of the multispecific antibody, and the nucleotide sequence represented by SEQ ID NO: 3 is a nucleotide sequence encoding the light chain of the antibody binding to Fn14 of the multispecific antibody. The amino acid sequence represented by SEQ ID NO: 2 is a polypeptide including the first VHH of the multispecific antibody encoded by SEQ ID NO: 1, the second VHH of the multispecific antibody, and the heavy chain of the antibody binding to Fn14 of the multispecific antibody, and the amino acid sequence represented by SEQ ID NO: 4 is the amino acid sequence of the light chain of the antibody binding to Fn14 of the multispecific antibody encoded by SEQ ID NO: 3. SEQ ID NOS: 5 to 12 are the amino acid sequences of exemplary peptide linkers. The nucleotide sequence represented by SEQ ID NO: 13 is a nucleotide sequence encoding the heavy chain of the antibody binding to Fn14, and the amino acid sequence represented by SEQ ID NO: 14 is the amino acid sequence encoded by the nucleotide sequence of SEQ ID NO: 13. The amino acid sequence represented by SEQ ID NO: 15 is the amino acid sequence of an antibody in which a mouse constant region is linked to the C terminal of the tandem VHH. The amino acid sequence represented by SEQ ID NO: 16 is the amino acid sequence of the heavy chain of the antibody binding to Fn14, and the amino acid sequence represented by SEQ ID NO: 17 is the amino acid sequence of the light chain of the antibody binding to Fn14. The amino acid sequence represented by SEQ ID NO: 18 is a polypeptide including the tandem VHH and the heavy chain of the antibody binding to Fn14.

The invention claimed is:

1. A polypeptide binding to ActRIIA and ActRIIB, wherein the polypeptide comprises a first VHH and a second VHH, binding to ActRIIA and ActRIIB, the first VHH comprises CDR1 consisting of the amino acid sequence of YGTMA (amino acid numbers 31 to 35 of SEQ ID NO: 2), CDR2 consisting of the amino acid sequence of TISGGGTTSYSDSVKG (amino acid numbers 50 to 65 of SEQ ID NO: 2), and CDR3 consisting of the amino acid sequence of RSIGTNDF (amino acid numbers 98 to 105 of SEQ ID NO: 2), and the second VHH comprises CDR1 consisting of the amino acid sequence of TNALI (amino acid numbers 172 to 176 of SEQ ID NO: 2), CDR2 consisting of the amino acid sequence of GIRADGRPYYGDSMKG (amino acid numbers 195 to 210 of SEQ ID NO: 2), and CDR3 consisting of the amino acid sequence of RLDDSG-TYD (amino acid numbers 243 to 251 of SEQ ID NO: 2).

2. The polypeptide according to claim 1, wherein the first VHH consists of the amino acid sequence of amino acid numbers 1 to 116 of SEQ ID NO: 2 and the second VHH consists of the amino acid sequence of amino acid numbers 142 to 262 of SEQ ID NO: 2.

3. The polypeptide according to claim 2, wherein the C terminal of the first VHH is linked to the N terminal of the second VHH via a peptide linker.

4. The polypeptide according to claim 3, wherein the polypeptide consists of the amino acid sequence of amino acid numbers 1 to 262 of SEQ ID NO: 2.

5. A polynucleotide comprising a nucleotide sequence encoding the polypeptide according to claim 1.

6. An expression vector comprising the polynucleotide according to claim 5.

7. A host cell transfected with the expression vector according to claim 6.

8. A method for producing a polypeptide capable of binding to ActRIIA and ActRIIB, the method comprising a step of culturing the host cell according to claim 7 to express the polypeptide.

9. A pharmaceutical composition comprising:

the polypeptide according to claim 1; and a pharmaceutically acceptable excipient.

10. A fused product composed of the polypeptide according to claim 1 and another peptide or protein.

11. A polynucleotide comprising a nucleotide sequence encoding the fused product according to claim 10.

12. An expression vector comprising the polynucleotide according to claim 11.

13. A host cell transfected with the expression vector according to claim 12.

14. A method for producing a fused product composed of a polypeptide binding to ActRIIA and ActRIIB and another peptide or protein, the method comprising a step of culturing the host cell according to claim 12 to express the fused product.

15. A pharmaceutical composition comprising:
the fused product according to claim 10; and
a pharmaceutically acceptable excipient.

* * * * *